US007625584B2

(12) United States Patent
Balasubramanian et al.

(10) Patent No.: US 7,625,584 B2
(45) Date of Patent: Dec. 1, 2009

(54) METHOD OF COMPLEXING A PROTEIN BY THE USE OF A DISPERSED SYSTEM AND PROTEINS THEREOF

(75) Inventors: Sathyamangalam V. Balasubramanian, Amherst, NY (US); Robert M. Straubinger, Amherst, NY (US); Karthik Ramani, Amherst, NY (US); Marc Besman, Studio City, CA (US); Ramesh Kashi, Walnut, CA (US)

(73) Assignee: The Research Foundation of State University of New York, Amherst, NY (US)

( * ) Notice: Subject to any disclaimer, the term of this patent is extended or adjusted under 35 U.S.C. 154(b) by 677 days.

(21) Appl. No.: 10/872,638

(22) Filed: Jun. 21, 2004

(65) Prior Publication Data
US 2005/0026242 A1    Feb. 3, 2005

Related U.S. Application Data

(63) Continuation-in-part of application No. 10/000,226, filed on Nov. 30, 2001, now abandoned, and a continuation-in-part of application No. 09/997,936, filed on Nov. 30, 2001, now abandoned.

(60) Provisional application No. 60/250,283, filed on Nov. 30, 2000, provisional application No. 60/250,137, filed on Nov. 30, 2000.

(51) Int. Cl.
    *A61K 9/127* (2006.01)
(52) U.S. Cl. .................. 424/450; 424/94.3; 435/174
(58) Field of Classification Search .............. 435/188; 530/350, 412, 427
See application file for complete search history.

(56) References Cited

U.S. PATENT DOCUMENTS

| | | | | |
|---|---|---|---|---|
| 4,196,191 A | * | 4/1980 | Almeida et al. | 424/450 |
| 4,965,344 A | * | 10/1990 | Hermann | 530/351 |
| 5,474,892 A | * | 12/1995 | Jakob et al. | 435/4 |
| 5,679,582 A | * | 10/1997 | Bowie et al. | 436/518 |
| 5,935,810 A | * | 8/1999 | Friedman et al. | 435/69.1 |
| 5,981,714 A | * | 11/1999 | Cheng et al. | 530/388.2 |
| 6,187,304 B1 | * | 2/2001 | Jin et al. | 424/85.5 |
| 6,245,359 B1 | * | 6/2001 | Milstein et al. | 424/490 |
| 6,447,800 B2 | * | 9/2002 | Hope | 424/450 |
| 6,528,325 B1 | * | 3/2003 | Hubscher et al. | 436/518 |
| 2002/0127635 A1 | | 9/2002 | Balasubramanian et al. | |
| 2002/0168734 A1 | * | 11/2002 | Grae | 435/173.1 |
| 2005/0026242 A1 | | 2/2005 | Balasubramanian et al. | |

FOREIGN PATENT DOCUMENTS

| | | | |
|---|---|---|---|
| WO | WO 9504524 A1 | * | 2/1995 |
| WO | WO 9955306 A1 | * | 11/1999 |
| WO | 0243665 A2 | | 6/2002 |
| WO | 02061036 A2 | | 8/2002 |
| WO | 2005017526 A1 | | 2/2005 |

OTHER PUBLICATIONS

Papahadjopoulos et al. "Sterically stabilized liposomes:Improvements in Pharmacokinetics and antitumor therapetuic efficacy" Proc. Nat. Acad. Sci NY (1991) 88: 11460-11464.*

Balasubramanian et al. :Liposomes as formulation excipeints for protein pharmaceuticals: A model protein study Pharm. Res. (2000) 17(3): 344-350.*

Yoshimoto et al. "Oxidative refolding of denatured/reduced lysozyme utilizing the chaperone-like function of liposomes and immobilized liposome chrmatagrphy" Biotechnol. Prog. (1999) 15: 480-487.*

Edelhoch, H. "The denaturation of Pepsin. III. The effects of various protein denaturancts on the kinetics of tpepsin inactivation" J. Am. Chem. Soc. (1958) 80: 6648-6655.*

Parodi et al. "Thermodynamics of unfolding of lysozyme in aqueous alcohol solutions" J. Biol. chem. (1973) 248(11): 4047-4051.*

Niclas et al. "Encapsulation and protection of the antibacterial enzyme, lysozyme, by unilamellar lipid vesicles," Book of Abstracts, 215th ACS National Meeting, Dallas, Mar. 29-Apr. 2 (1998), CHED-394 Publisher: American Chemical Society, Washington, D. C. (downloaded from STN Sep. 17, 2008).*

Kuboi et al. "Refolding pf carbonic anhydrase assisted by 1-palmitoyl-2-oleoyl-sn-glycero-3-phosphocholine liposomes" Biotecnol. Prog. (1997) 13: 828-83.*

* cited by examiner

*Primary Examiner*—Irene Marx
*Assistant Examiner*—Susan Hanley
(74) *Attorney, Agent, or Firm*—Hodgson Russ LLP

(57) ABSTRACT

The present invention relates to methods for complexing a protein in a dispersed medium. Also disclosed are associated proteins produced by the methods of complexing of the present invention. Pharmaceutically effective stabilized protein dosages are also disclosed. The present invention also relates to a method for associating AHF protein in a dispersed medium.

16 Claims, 20 Drawing Sheets

Native Protein ↔ SI$_1$ → SI2 → SI3

↑↓   ↓↑

Soluble aggregates→→ Precipitation.

METHOD OF COMPLEXING A PROTEIN BY THE USE OF A DISPERSED SYSTEM AND PROTEINS THEREOF

This is a continuation-in-part of U.S. application Ser. No. 10/000,226, filed on Nov. 30, 2001 now abandoned, which claims the benefit of U.S. Provisional Application Ser. No. 60/250,283, filed on Nov. 30, 2000, and U.S. application Ser. No. 09/997,936, filed on Nov. 30, 2001 now abandoned, which claims the benefit of U.S. Provisional Patent Application Ser. No. 60/250,137, filed on Nov. 30, 2000 (all of which are hereby incorporated by reference in their entirety).

BACKGROUND OF THE INVENTION

1. Field of the Invention

The present invention relates to methods for complexing a protein in a dispersed medium, a method for complexing AHF protein in a dispersed medium, an associated protein produced by the methods of complexing a protein in a dispersed medium, and pharmaceutically effective stabilized protein dosages.

2. Description of the Related Art

Advances in protein engineering have led to the large scale production of proteins and peptides for pharmaceutical purposes. However, for many proteins, the preservation of higher order structure, such as secondary, tertiary and quaternary conformation, is necessary to retain activity. The formulation of such suitable protein and peptide based pharmaceuticals is largely an unsolved problem. Proteins undergo physical and chemical instability, and these instabilities present unique difficulties in the production, formulation, and storage of protein pharmaceuticals (Ahern et al., *Pharmaceutical Biotechnology*, Borchardt, Ed., pp 550, Plenum Press, New York (1992); Balasubramanian et al., *Pharmaceutical Research* 17:343-349 (2000)). Denaturation, aggregation, and precipitation are frequent manifestations of physical instability.

Other pharmaceutical concerns of the protein products are shorter half-life and immune response following prolonged use of the drug (Ahern et al., *Pharmaceutical Biotechnology*, Borchardt, Ed., pp 550, Plenum Press, New York (1992)). Delivery vehicles, such as liposomes, have been explored to improve stability, to prolong the circulation time, and to alter the immunogenecity issues (Balasubramanian et al., *Pharmaceutical Research* 17:343-349 (2000)). It is known that when liposomes are added to proteins, the stability of proteins are improved since liposomes help reduce the amount of aggregation of the protein. However, the liposomes typically complex with only a small percentage of the total protein. Accordingly, the pharmaceutical developments of such delivery vehicles are hampered by poor association with proteins.

Thus, there is a need for suitable protein and peptide based pharmaceuticals having improved stability during processing and storage conditions; increased dosage spacing by increasing bioavailability, thus reducing cost and patient discomfort; easy handling; and improved delivery to the site of vascular damage. The present invention is directed to overcoming these and other deficiencies in the art by providing a methodology to engineer a complex between a protein and a dispersed system based delivery vehicle.

SUMMARY OF THE INVENTION

One aspect of the present invention relates to a method for complexing a protein in a dispersed medium. This method involves providing a protein and altering the conformational state of the protein to expose hydrophobic domains therein. A stabilizer is bound to the exposed hydrophobic domains. The alteration is at least partially reversed to associate at least a portion of the protein with the stabilizer.

Another aspect of the present invention relates to an associated protein produced by providing a protein, altering the conformational state of the protein to expose hydrophobic domains therein, binding a stabilizer to the exposed hydrophobic domains, and at least partially reversing the alteration to associate at least a portion of the protein with the stabilizer.

A further aspect of the present invention relates to a pharmaceutically effective stabilized protein dosage, in which less than about 1% to greater than about 90% of the protein is associated with the stabilizer.

Yet, another aspect of the present invention relates to a method for associating AHF protein in a dispersed medium. This method involves providing an AHF protein and altering the conformational state of the AHF protein to expose hydrophobic domains therein. A stabilizer is bound to the exposed hydrophobic domains. The alteration is at least partially reversed to associate at least a portion of the protein with the stabilizer.

Still, another aspect of the present invention relates to a dispersion system-associated AHF protein produced by providing an AHF protein and altering the conformational state of the AHF protein to expose hydrophobic domains therein. A stabilizer is bound to the exposed hydrophobic domains. The alteration is at least partially reversed to associate at least a portion of the protein with the stabilizer.

Yet, a further aspect of the present invention relates to a pharmaceutically effective stabilized AHF dosage, wherein above about 0.5%, preferably above about 3%, and more preferably above about 25% of the AHF is associated with a stabilizer.

Another aspect of the present invention relates to a method for complexing a protein in a dispersed medium. This method involves providing a protein and altering a conformational state of the protein to expose hydrophobic domains therein by contacting the protein with a mixture comprising ethanol at a concentration of about 10-50%. A stabilizer is bound to the exposed hydrophobic domains. The alteration is at least partially reversed to associate at least a portion of the protein with the stabilizer.

These and other aspects of the present invention will become apparent upon a review of the following detailed description and the claims appended thereto.

BRIEF DESCRIPTION OF THE DRAWINGS

FIG. 12 is a schematic representation of the folding characteristics of rhAHF and its relation to physical instability pathways.

DETAILED DESCRIPTION OF PREFERRED EMBODIMENTS

The present invention employs the use of a solvent, such as ethanol, in a concentration of about 10-50%, to alter the conformation of a protein in order to form structures that are suitable for triggered loading (i.e., to engineer a hydrophobic interaction between a protein and dispersed system, such as liposomes). These structures are distinctly different from conventional intermediate structures such as molten globules. Conventional intermediate structures lack tertiary structural features, but pose substantial secondary structural features. In contrast, ethanol-mediated structures utilized in the present invention have substantial tertiary and secondary structural features.

One aspect of the present invention relates to a method for complexing a protein in a dispersed medium. This method involves providing a protein and altering the conformational state of the protein to expose hydrophobic domains therein. A stabilizer is bound to the exposed hydrophobic domains. The alteration is at least partially reversed to associate at least a portion of the protein with the stabilizer.

Another aspect of the present invention relates to an associated protein produced by providing a protein, altering the conformational state of the protein to expose hydrophobic domains therein, binding a stabilizer to the exposed hydrophobic domains, and at least partially reversing the alteration to associate at least a portion of the protein with the stabilizer.

A further aspect of the present invention relates to a pharmaceutically effective stabilized protein dosage, in which less than about 1% to greater than about 90% of the protein is associated with the stabilizer.

Another aspect of the present invention relates to a method for complexing a protein in a dispersed medium. This method involves providing a protein and altering a conformational state of the protein to expose hydrophobic domains therein by contacting the protein with a mixture comprising ethanol at a concentration of about 10-50%. A stabilizer is bound to the exposed hydrophobic domains. The alteration is at least partially reversed to associate at least a portion of the protein with the stabilizer.

Figure 5A:
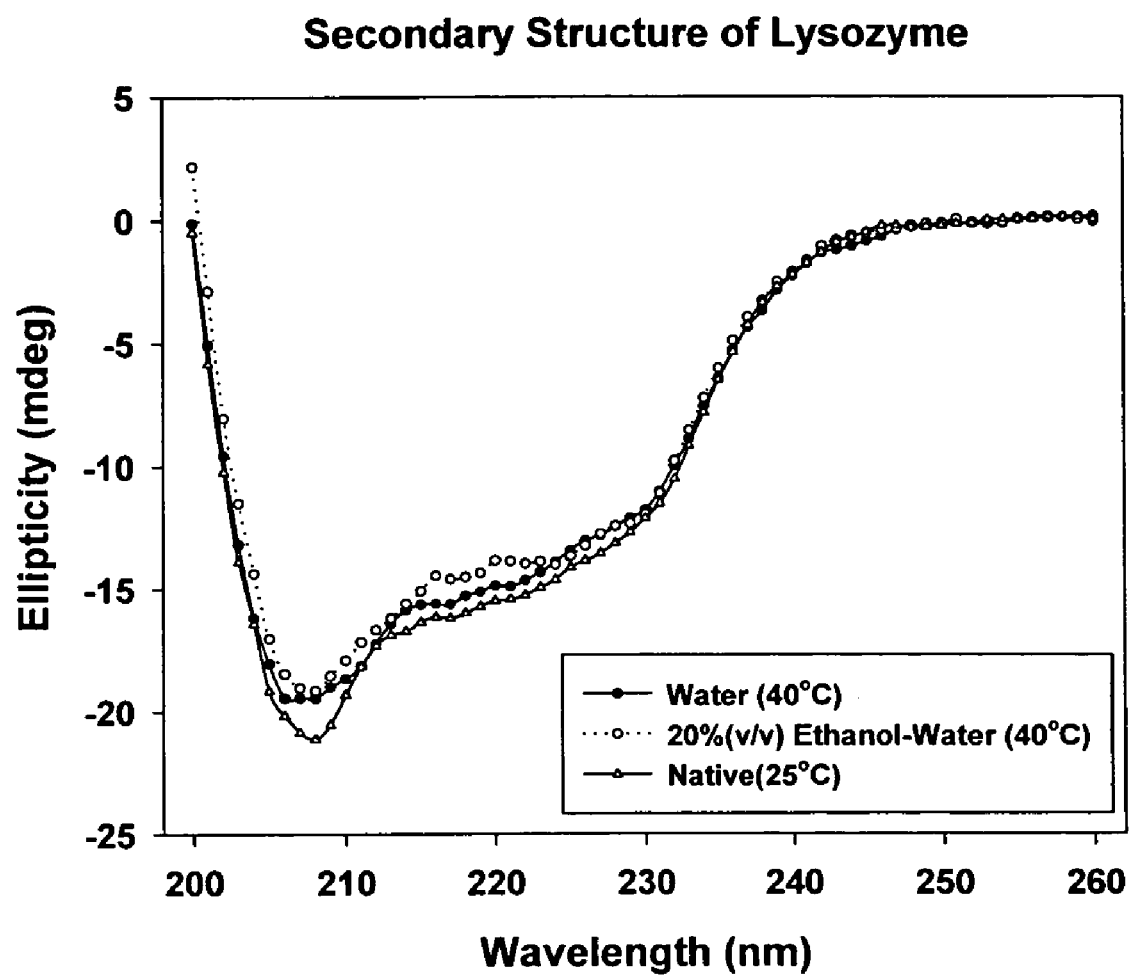
FIG. 5A shows the secondary structures of lysozyme at different protein concentrations ranging from 1.40 µM to 47.5 µM in water in the presence and in the absence of 20% ethanol.
Figure 5B:
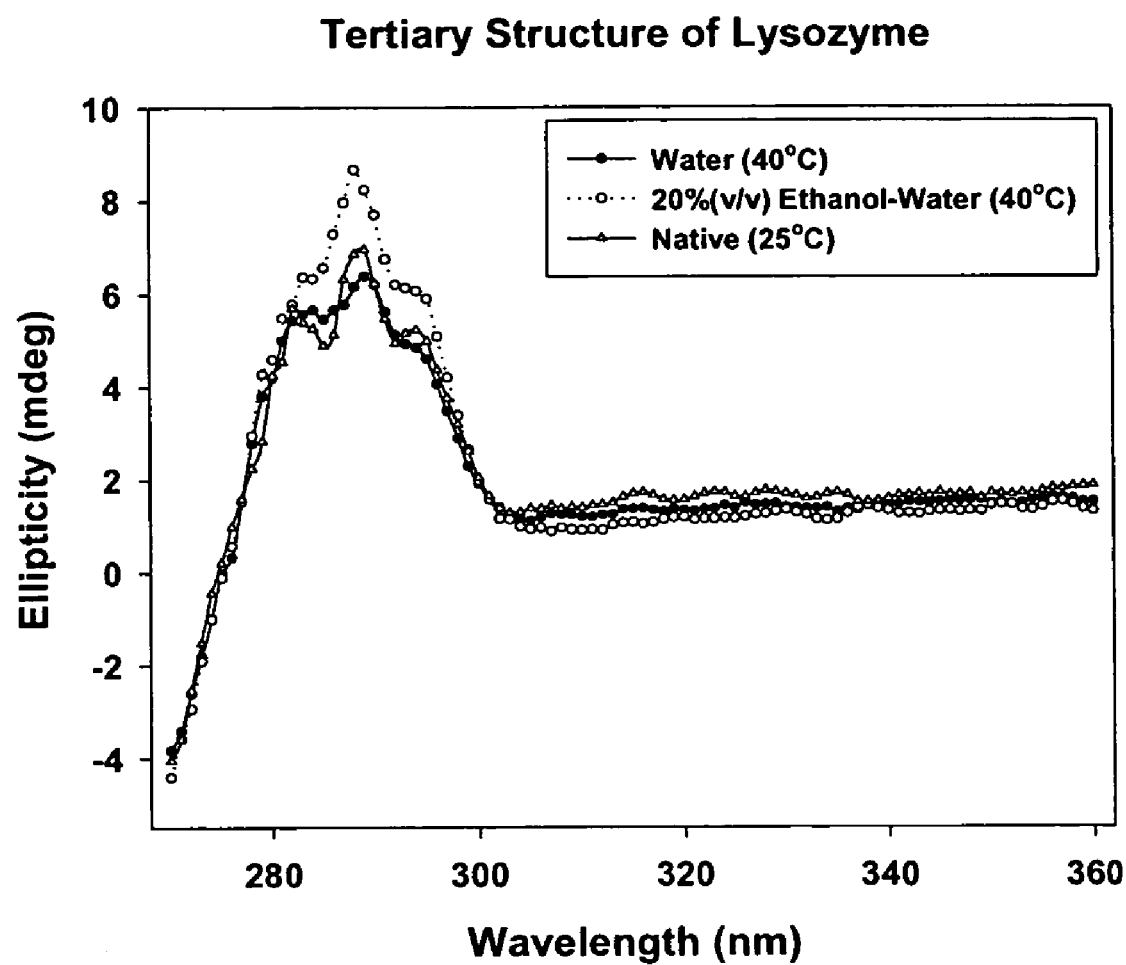
FIG. 5B shows the tertiary structures of lysozyme at different protein concentrations ranging from 1.40 µM to 47.5 µM in water in the presence and in the absence of 20% ethanol.

In general, the present invention relates to a method for engineering the complexation of protein with a dispersed system and the complexed proteins prepared therefrom. A dispersed system is considered any system having a hydrophobic interior and a hydrophillic exterior. A stabilizer or excipient is added at the desired stage during an alteration in the conformational state of a protein. For example, it is added to a partially folded protein under controlled protein unfolding conditions. The structures of the partially folded protein under the methods of the present invention are distinct from conventional intermediate structures such as molten globules. Whereas the conventional intermediate structures lack tertiary structural features but have substantial secondary structures, the structures utilized in the present invention poses substantial secondary and tertiary structures. For example, the near and far UV CD of protein in the presence of a 20% ethanol at 40° C. (FIG. 5B) show substantial tertiary structural features. In addition, under these solution conditions, the exposure of hydrophobic domains is higher than that of thermal stress alone (FIG. 2). This may be due to the interaction of ethanol with protein that promotes the clustering of solvent molecules around hydrophobic groups. Such interaction has been shown to result in lowering of transition temperature (TM)(Remmele et al., *Biopharm.* 2000, 36-46, which is hereby incorporated by reference in its entirety). At higher alcohol concentrations, helical structures were formed (Bhakuni, *Archives of Biochemistry and Biophysics* 357:274-284 (1998), which is hereby incorporated by reference in its entirety). Proteins formulated with lower alcohol concentrations are preferable for parenteral dosage forms in order to prevent adsorption of proteins to surfaces, provide easy handling of the proteins. Moreover, proteins formulated with less than about 50% alcohol concentrations are safer for human use and have an increased likelihood of activity because the structures are more native-like.

The interaction of conventional intermediates with membranes has been described (Yoshimoto et al., *Biotechnol. Prog.* 15:480-487 (1999); Banuelos et al., *Journal of Biological Chemistry* 270:29910-29915 (1995), which are hereby incorporated by reference in their entirety). However, use of the off pathway structures of the present invention in mediating encapsulation by exposed hydrophobic domains has not been described.

In accordance with the present invention, the conformational state of a protein is altered to expose hydrophobic domains. The hydrophobic domains of a protein are exposed to enhance the ability of a stabilizer to associate with the protein. Association includes encapsulation. Unfolding in the presence of alcohol, preferably ethanol, is a preferred method for altering conformational states of proteins. Such complexation is engineered to enhance the hydrophobic interaction and translocation of a protein in a dispersed system in an effort to increase the association efficiency of the protein. Activity is retained by the preservation of higher order structure of a protein, such as secondary, tertiary, quaternary conformations, and/or intermediate conformational structures thereof. In this manner, problems of physical and chemical instability such as denaturation, aggregation, and precipitation can be overcome by leading to improvements in production, formulation, and storage of protein pharmaceuticals.

In the present invention, protein structural conformational changes, may include native-like secondary structures (in the presence of ethanol), secondary protein structure, intermediate or secondary-tertiary hybrid protein structure changes, tertiary protein structure changes, and/or quaternary protein structure changes, etc.

Experimentally, the secondary, tertiary, and/or quaternary structures (i.e., which experimentally include intermediate protein structure conformations, such as secondary-tertiary hybrid protein structures, etc.) of the protein are monitored under conformational altering conditions, which include unfolding. For example, the exposure of hydrophobic domains is confirmed by binding of a specific fluorescence probe to the exposed hydrophobic domains. In this manner, such experiments are used to identify specific conformational states of a protein with exposed hydrophobic domains. Upon exposure of the desired hydrophobic domain, the stabilizer is added.

In general, specific conformational states with exposed hydrophobic domains may be generated by subjecting proteins to heat (i.e., temperatures above the temperature optimum of a known protein), cold temperature (i.e., below the temperature optimum of a known protein), organic and inorganic solvents, co-solvent mixtures, and co-solutes under varying pH conditions.

In a preferred embodiment, the methods of the present invention are carried under conditions in which the temperature of the protein is between 40° C. and 74° C.

In accordance with the present invention, a methodology is presented to engineer a complex between the protein and the dispersed system based delivery vehicle, which overcomes problems typically associated with shorter half-life and immune response following prolonged use of a drug by improving stability and prolonging the circulation time of the drug. In particular, the present invention solves the pharmaceutically related problems stemming from the use of liposomes as delivery vehicles generally attributed to poor association of proteins.

According to the methodology of the present invention, such a protein was subject to conditions which changes the conformation of the protein to expose its hydrophobic domains and then to associate at least a portion of the protein with a stabilizer. The present formulation strategy exploits the conformational changes induced by alcohols, such as ethanol, and/or properties of the intermediate structures of a protein. The first step is to form "structured" intermediate states using alteration in the conformational state, such as controlled unfolding of the protein. Conditions are controlled carefully, enabling the exposure of domains that permit interaction with the excipient.

The present invention is not limited by the choice of protein. Any protein would be applicable, which includes, but is not limited to, biopolymers composed of natural and unnatural amino acids, and multi-domain proteins.

Also, the present invention is not limited by the choice of protein concentration, any protein concentration would be applicable. Suitable protein concentrations for use in methods of the present invention include concentrations from about 14 μM to about 47.5 μM.

In particular, lysozyme was used as an example of a protein applicable to the methods of the present invention to investigate the use of a solvent for complex formation in a dispersed system.

Lysozyme was chosen as a representative protein for the following reasons. Lysozyme is a hydrophilic protein and its spontaneous encapsulation in neutral liposomes is limited. Significantly, thermal stress of a protein in aqueous systems do not generate intermediate structures, but such structures are observed in ethanol-water mixtures.

Lysozyme is a bacteriolytic protein which is under investigation as a therapeutic agent for AIDS (Tavio et al., *Eur. J. Cancer* 34:1634-1637 (1998); Lunardi-Iskandar et al., *Nat. Med.* 4:428-434 (1998); Witzke et al., Eur. J. Med. Res. 2:155-158 (1997), which are hereby incorporated by reference in their entirety). It has been shown that the transmission of HIV type I from mother to fetus in the first trimester is prevented by hcg beta subunit and lysozyme present in hcg b core preparations (Lunardi-Iskandar et al., *Nat. Med.* 4:428-434 (1998); Lee-Huang et al., *Proc. Natl. Acad. Sci. USA* 96:2678-2681 (1999), which are hereby incorporated by reference in their entirety). Recently, Lee-Huang et al. (*Proc. Natl. Acad. Sci. USA* 96:2678-2681 (1999), which is hereby incorporated by reference in its entirety) have shown that lysozyme obtained from other sources such as human milk and chicken egg white also possess activity against HIV-1. Detailed structural information is available to investigate structure-stability relationships of lysozyme.

For purposes of the present invention, liposomes are defined as microcapsules having a hydrophobic interior and a hydrophillic exterior synthesized from lipids. Stabilizers suitable for use in the present invention include such liposomes. Other suitable dispersed systems include micelles, detergents, and the like.

The composition of the liposomes can be modified to enhance the association with the native state, thus preventing denaturation. Liposomes may also interact with intermediate states without altering the refolding appreciably, thereby exerting a beneficial effect through stabilization of the intermediate states or inhibiting progression to conformations that lead to other physical instabilities, such as aggregation. Alternatively, the liposomes may act as chaperones, assisting the protein to refold to a state that resembles more closely the native structure. Finally, liposomes may guide the protein refolding to unique intermediate structures that are stabilized and active, yet different from the folding intermediates that would exist in the absence of the liposomes.

The present invention enables the liposome association of from less than about 1% to greater than about 90% of the lysozyme protein, preferably above about 1%, more preferably above about 3%, more preferably from about 3% to about 90%, and most preferably from about 80% to about 90% of the protein. It is understood that the % association, including encapsulation, is related in part to the size of the protein, and the specific % association for a given protein will vary accordingly with different size proteins.

The present invention is applicable to any method suitable for changing the structural or conformational state of the protein to expose its hydrophobic domains, unfolding being preferred. While the use of solvents as a perturbant for the complex formation has been chosen as an example, the present invention is not limited to this method alone. For example, the use of solvents in combination with heat will typically expedite the changing of the conformational state of the protein.

Changing the conformational state, such as unfolding, of the protein to expose its hydrophobic domains is possible by both chemical and/or physical perturbants.

In general, physical perturbants include, but are not limited to, thermal changes and/or pressure changes. For example, thermal changes include specific temperature ranges. For methods of the present invention, a preferred temperature range is from about 25° C. to about 95° C.

Chemical perturbants include, but are not limited to, chemical solvents (i.e., organic or inorganic solvents), co-solvent mixtures, co-solutes and the like. Chemical solvents include, but are not limited to, organic solvents, such as non-water based liquids (e.g., ethanol), inorganic solvents, and the like.

Co-solvents include, but are not limited to, solvent and water mixtures in different proportions (e.g., mixtures of ethanol and water) and buffer solutions (i.e., such as buffers with acidic or basic pH).

In accordance with the present invention, ethanol solvents used in the present invention, include any commercially available grade, which includes, but is not limited to, denatured ethanol, 190 Proof reagent grade ethanol, denatured reagent grade, and/or 200 Proof reagent grade ethanol.

Moreover, different ethanol-water mixtures include, but are not limited to, ethanol-water solutions, and/or ethanol-phosphate buffered saline solutions (ethanol-PBS). The ethanol content in such ethanol-water mixtures are present in a range from about 3% ethanol to about 80% ethanol, with a preferable range from about 20% ethanol to about 80% water, more preferably in a range from about 20% ethanol to about 40% ethanol.

Buffer solutions suitable for use in the present invention include, but are not limited to, phosphate buffer solution, saline, Tris-HCl, water, and the like.

Co-solutes include other chemical components and/or molecules in solution along with a protein of the present invention, which includes, but is not limited to, organic compounds (e.g., urea or conventional detergents) and inorganic compounds and/or salts, which correspond to aforementioned organic/inorganic compounds (e.g., ions such as $Na^+$, Guanidine hydrochloride, etc.). Several organic solvents are compatible with protein and include, but are not limited to, alcohols, such as methanol, ethanol, glycerol, ethylene glycol, and the like.

In accordance with the present invention, it was determined that use of different experimental conditions based upon the different types of chemical and/or physical perturbants significantly affected the different protein conformation states and/or characteristics experimentally observed.

In particular, it was determined that protein complexation with different chemical perturbants, stabilizers, excipients, solutions, etc., such as those defined above, occurs under different experimental conditions, achieved by use of chemical or reagent grade solvents (i.e., ethanol or other chemical solutions) as commercially available, and/or different buffer solutions at a different pH or within a pH range and at different protein concentrations as indicated therein.

For methods of the present invention, a suitable pH may have a specific value from about 6 to about 8, such as a pH of 7.4. Methods of the present invention also may be conducted within a suitable pH range from about 6 to about 8.

Figure 1A:
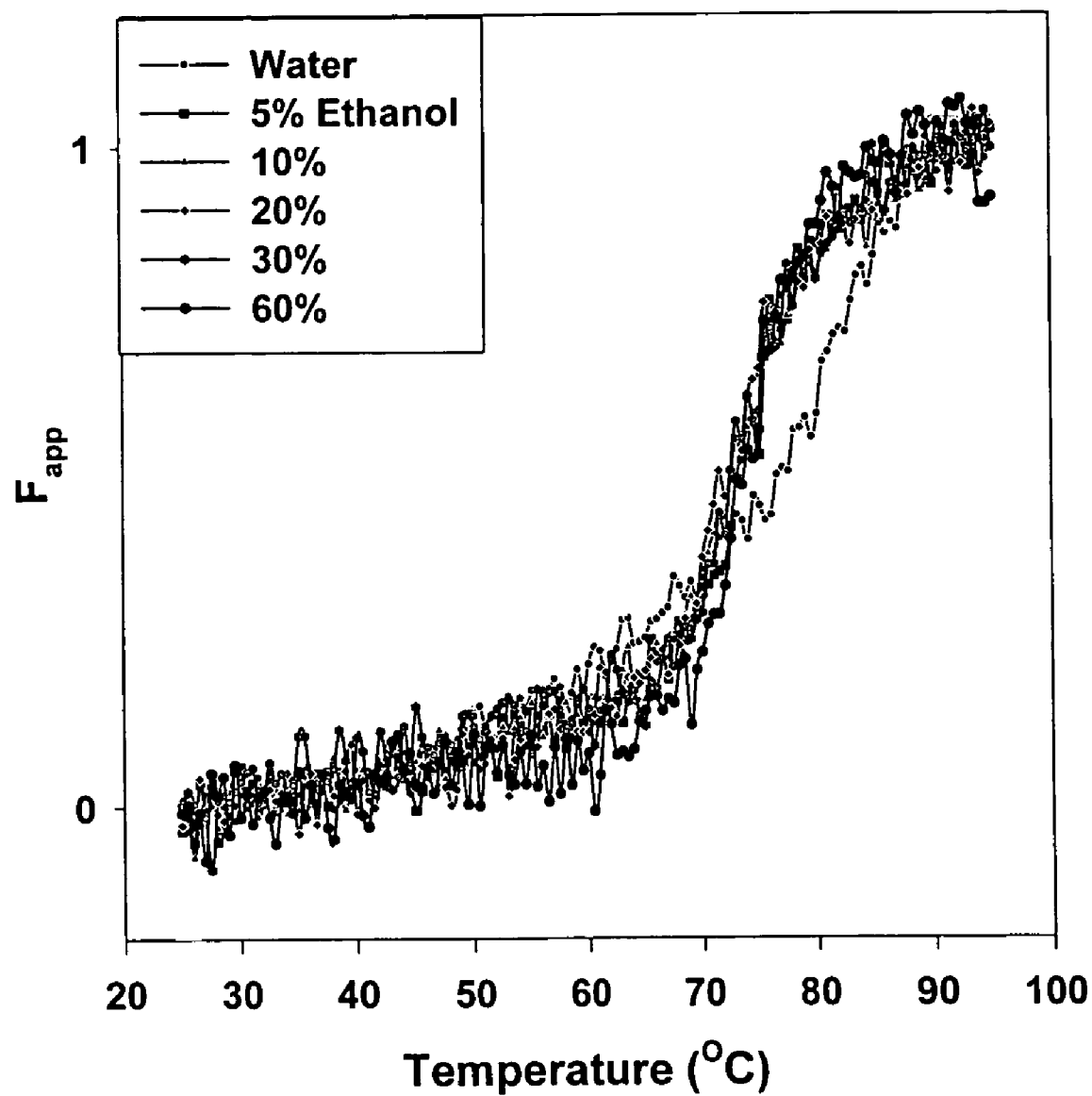
FIG. 1A shows the temperature dependent changes in the secondary structure of lysozyme in ethanol-water mixtures by plotting ellipticity at 220 nm and 268 nm as a function of temperature.
Figure 1B:
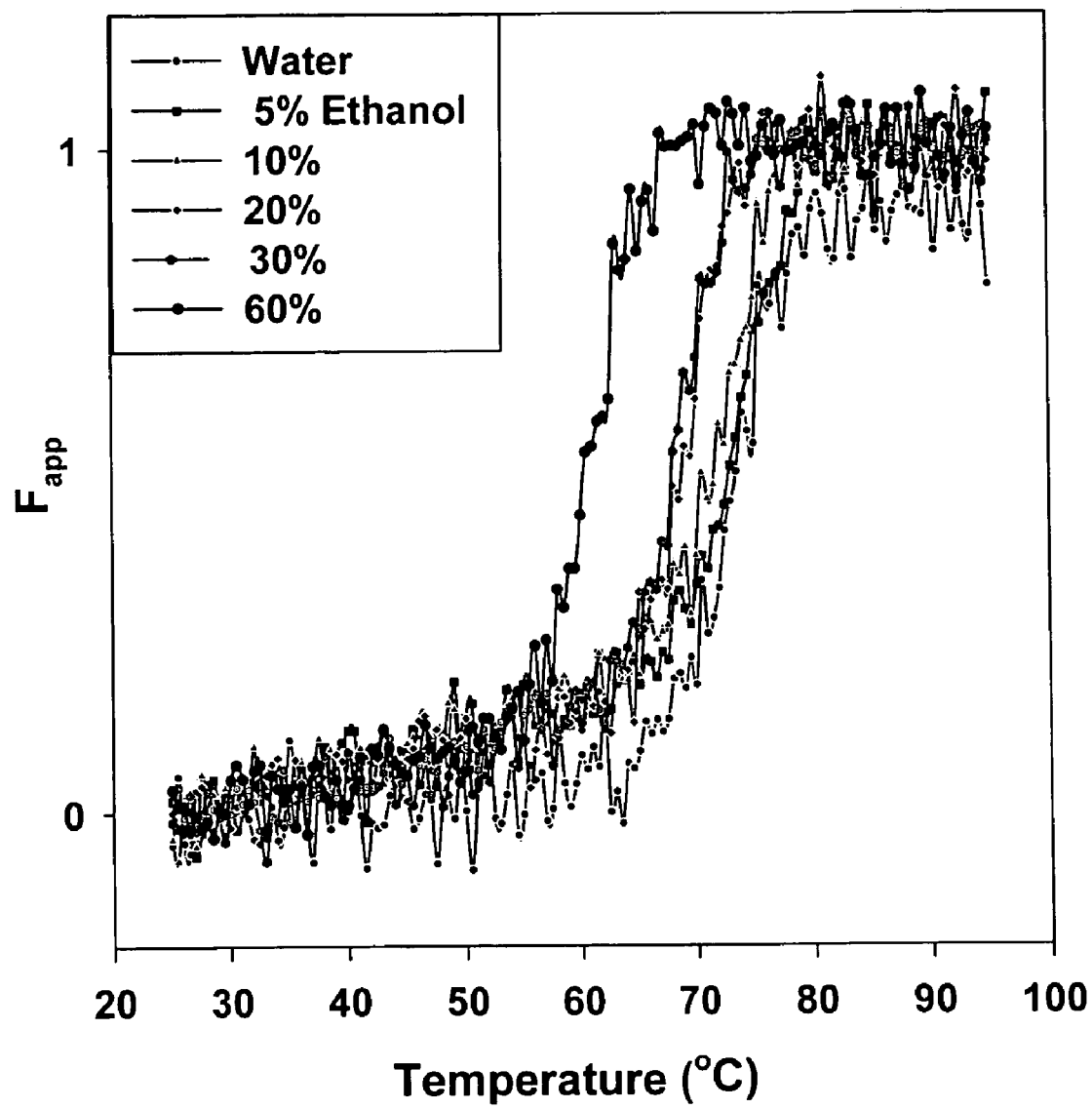
FIG. 1B shows the temperature dependent changes in the tertiary structure of lysozyme in ethanol-water mixtures by plotting ellipticity at 220 nm and 268 nm as a function of temperature.

Lysozyme was subjected to thermal stress in ethanol-water mixtures to generate intermediate structures. In water, the melting curve obtained for tertiary and secondary structural changes overlap (Tm of 74° C.)(FIGS. 1A and 1B). These data indicate that there are no intermediates in water, but the thermal stress of lysozyme in ethanol-water generated secondary-tertiary hybrid or intermediate structures. Such conclusions were drawn based on the melting profiles in which the Tm measured by secondary and secondary structures do not overlap (FIGS. 1A and 1B).

Figure 4A:
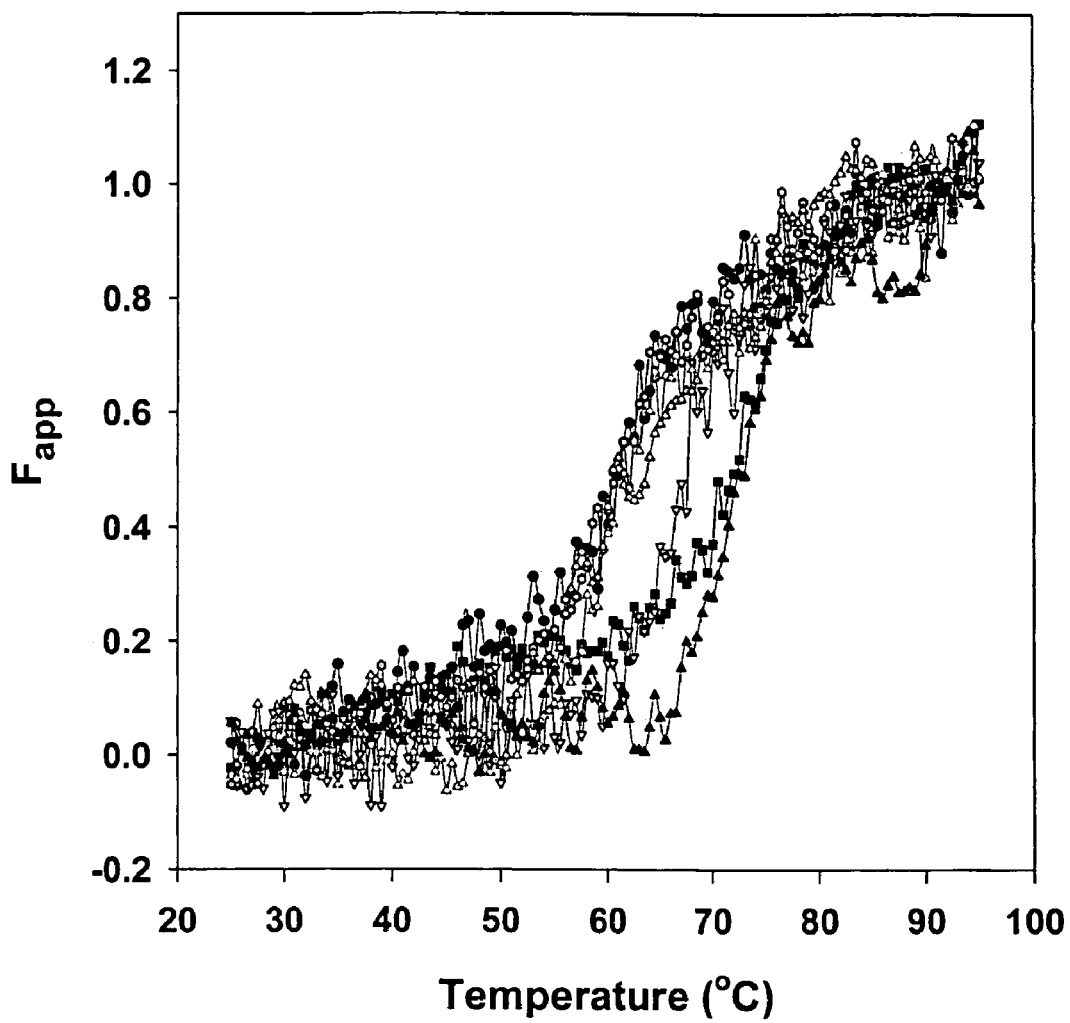
FIG. 4A shows the temperature dependent changes in the secondary, secondary-tertiary hybrid or intermediate, and tertiary structures of lysozyme at different protein concentrations ranging from about 1.40 µM to about 47.5 µM, in different ethanol-water mixtures with ethanol percentage ratios from about 20% ethanol to about 40% ethanol by plotting ellipticity at wavelengths of 220 nm and 290 nm as a function of temperature.
Figure 4A:
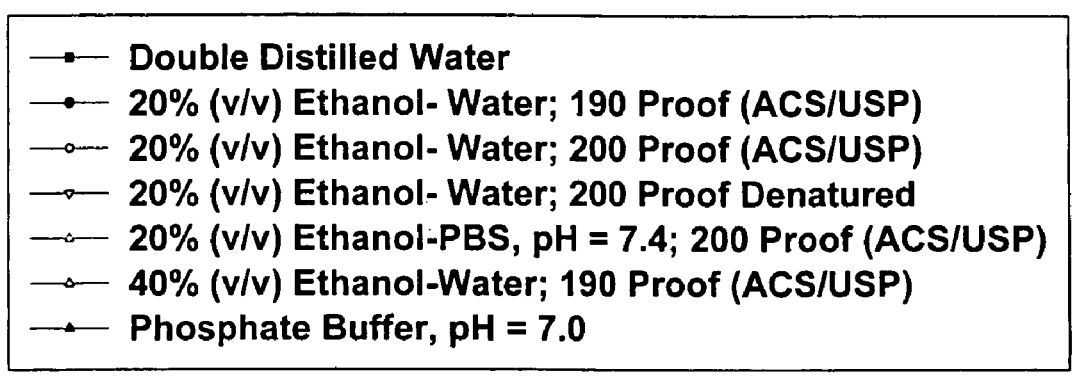
Figure 4B:
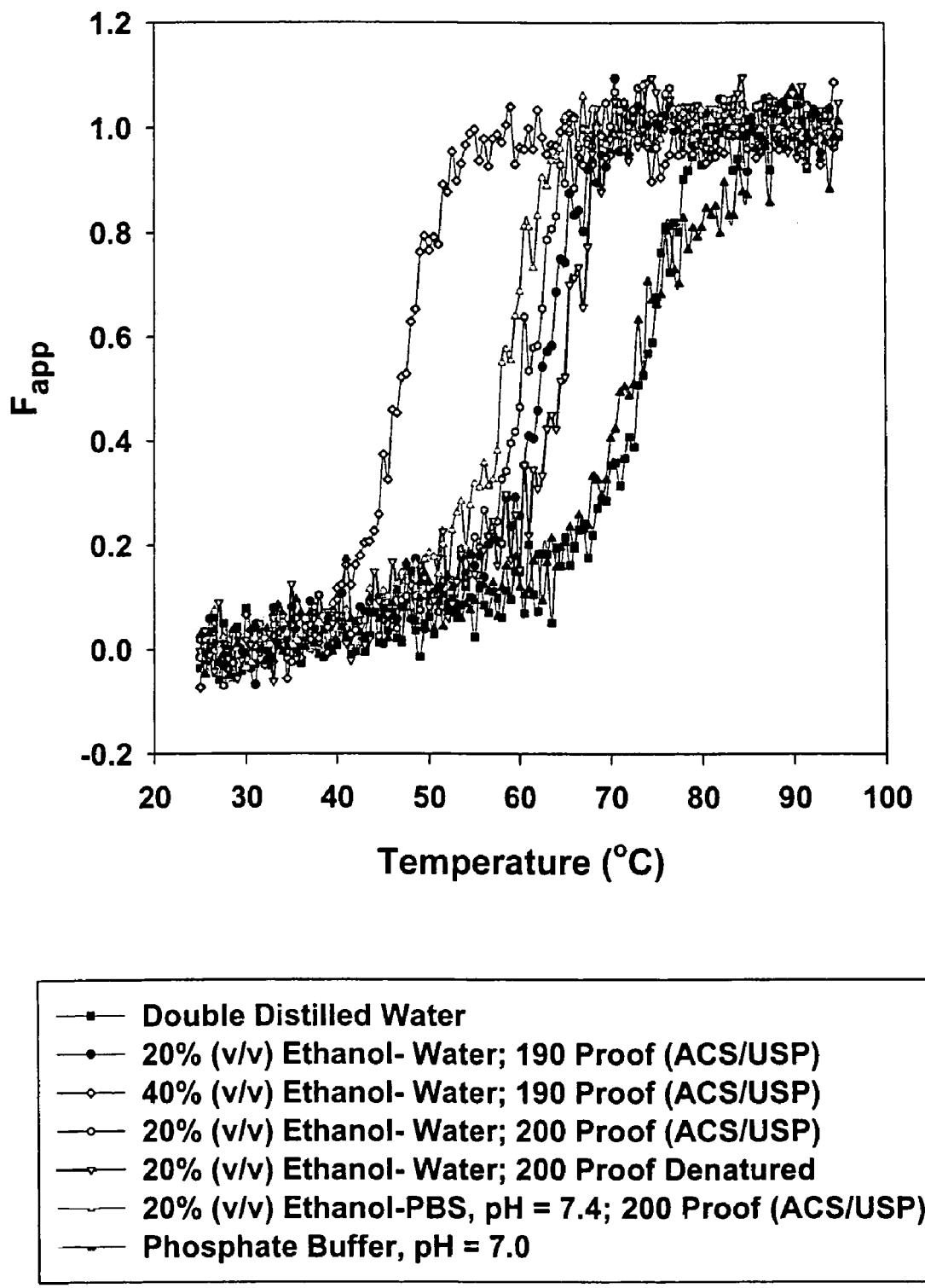
FIG. 4B shows the temperature dependent changes in the tertiary structure of lysozyme in ethanol-water mixtures by plotting ellipticity at wavelengths of 220 nm and 290 nm as a function of temperature.

In order to investigate the effect of ethanol on unfolding of the protein, thermal denaturation studies were carried out for lysozyme in ethanol-water mixtures. Addition of ethanol as low as 5%, decreased the Tm (s) measured by secondary structural changes by 2° C. (FIGS. 1A and 4A). However, the Tm (t) measured by monitoring the tertiary structure decreases as the ethanol concentration was increased (FIGS. 1B and 4B). At lower ethanol concentrations, such as from 0% to 10%, the midpoint of the melting profile measured by secondary and tertiary structure overlap; Tm (s) and Tm (t) were equal but as the ethanol concentration was increased, the difference between Tm (s) and Tm (t) increased (FIGS. 1A-B and FIGS. 4A-B). For example, in the presence of 20% ethanol, Tm (s) was found to be 72.5° C., whereas Tm (t) is 68° C. (FIGS. 1A-B and FIGS. 4A-B).

In addition, in the presence of 20% ethanol at 70° C., lysozyme lost all of its tertiary structural characteristics, but has substantial residual secondary structural features. At 70° C., lysozyme displays the properties of intermediate states (FIGS. 4A and 4B, which show data results which explain such results as based upon different experimental conditions, i.e., different reagent grades of ethanol, defined pH conditions and different lysozyme material batches).

In the temperature range of from about 68° C. to about 72.5° C., the protein displays the properties of an intermediate state. This intermediate structure exposes the hydrophobic domains suitable for complex formation. The exposure of hydrophobic domain can also be achieved by the addition of ethanol. For example, in the temperature range of 30° C. and 50° C., ethanol does not alter the conformation of the protein as is indicated by the native like CD profiles, but promotes the exposure of hydrophobic domains. The observed ethanol induced conformational changes or generation of intermediate structure, may be due to the interaction of the solvent with protein. Timasheff and Inoue (*Biochemistry* 7:2501-2513 (1968), which is hereby incorporated by reference in its entirety) suggested that addition of third component to a binary (protein-water system) have important effects on the forces that stabilize the native and altered structure of the proteins. As a protein unfolds, the non-polar residues come into contact with the solvent system. In this process, the organic component used as an additive tends to cluster about these residues. Thus, in the presence of ethanol exposure of few hydrophobic residues may be thermodynamically favored.

The observed off pathway unfolding profile induced by ethanol may be due to its interaction with protein (Bhakuni, *Archives of Biochemistry and Biophysics*, 357:274-284 (1998), which is hereby incorporated by reference in its entirety). The interaction of alcohol with proteins has been extensively investigated. Timasheff and Inoue (*Biochemistry* 7:2501-2513 (1968), which is hereby incorporated by reference in its entirety) suggested that addition of third component to a binary (protein-water) system have important effects on the forces that stabilize the native and altered structure of proteins. As a protein unfolds, the non-polar residues come into contact with the solvent system. In this process, the organic component used as an additive tends to cluster about these residues. Thus, in the presence of ethanol, exposure of few hydrophobic residues may be thermodynamically allowed and these contacts may not be favored in hydrophilic environments.

Further, the solvent based excipients may provide easier pharmaceutical processing and handling conditions during isolation, shipping, storage and administration of the therapeutic proteins. Apart from ethanol, other solvents such as glycerol, have been shown to be compatible for the stability of lysozyme (Rariy et al., *Biotechnol. Bioeng.* 62:704-710 (1999); Rariy et al., *Proc. Natl. Acad. Sci. USA* 94:13520-13523 (1997); Knubovets et al., *Proc. Natl. Acad. Sci. USA* 96:1262-1267 (1999), which are hereby incorporated by reference in their entirety). In addition, other pharmaceutically acceptable solvents, such as propylene glycol, may be suitable candidates for the development of protein pharmaceuticals as they are well tolerated for subcutaneous administration. This is because most of the proteins are subcutaneously administered.

Antihemophilic ("AHF") protein was also used as an example of a protein applicable to the methods of the present invention to investigate the use of a solvent for complex formation in a dispersed system.

Recent advances in biotechnology and protein engineering, together with cloning of the gene coding for AHF (Toole et al., *Nature* 312:342-7 (1984); Wood et al., *Nature* 312: 330-7 (1984), which are hereby incorporated by reference in their entirety), have made it feasible to manufacture recombinant human AHF ("rhAHF"). The recombinant preparation promises to be a source of unlimited supply, together with the freedom from the complications of transmission of blood-borne viruses. However, the commercially available protein pharmaceutical has been reported to undergo the aforementioned physical instability problems with concomitant loss of therapeutic activity, thus requiring a new formulation strategy. This requires an understanding of its complex structure and dynamic folding features. Structurally, the AHF can be divided into a heavy chain, including domains A1 and A2, and a light chain, including domains A3, C1 and C2. The heavy and the light chains are connected in space by a third distinct B domain (Fay, *Thromb. Haemost.* 70:63-7 (1993); Foster et al., *Blood Rev* 3:180-91 (1989), which are hereby incorporated by reference in their entirety). However, the important features related to the folding behavior of this large multidomain protein are unknown in the art, and may be an integral part of an effective approach towards development of a stable formulation.

Recombinant human factor VIII (AHF) is a multi-domain protein used in the treatment of patients with classical Hemophilia A. Because of its complex structure and folding characteristics, the present clinical formulation has several disadvantages; (1) formulations show physical instability, denaturation of the protein promoting aggregation that is associated with the concomitant loss of activity (2) formulations have a short half life in circulation, requiring frequent administration of the drug and (3) formulations illicit immune response requiring higher doses of frequent administration. This translates into not only higher cost but also patient discomfort.

In order to overcome the above-noted problems, the present invention provides a method wherein the Antihemophilic protein is associated with the dispersion system, such as liposomes, through complex association, including encapsulation by the liposomes.

Thus, another aspect of the present invention relates to a method for associating AHF protein in a dispersed medium. This method involves providing an AHF protein and altering the conformational state of the AHF protein to expose hydrophobic domains therein. A stabilizer is bound to the exposed hydrophobic domains. The alteration is at least partially reversed to associate at least a portion of the protein with the stabilizer.

A further aspect of the present invention relates to a pharmaceutically effective stabilized AHF dosage, wherein above about 0.5%, preferably above about 3%, and more preferably above about 25% of the AHF is associated with a stabilizer.

Since AHF is a multidomain protein several intermediates are possible and the association of a specific intermediate may be advantageous over another. This is most likely due to the association of a specific region of the protein which may influence several aspects, such as protein refolding, and provide less immune response due to the association of the C2 domain. The use of a combination of perturbants, solvent and heat, to enhance the effect and achieve exposure at lower temperatures is also provided by the present invention, as is stabilization of the AHF complex with hydrophobic domain interaction.

Since the process of denaturation is related to an alteration in the conformational state of the protein antihemophilic factor (AHF/factor VIII), used in the treatment of Hemophilia A, such as unfolding at the molecular level, the conformational changes as the protein unfolds were analyzed and novel methods at key steps in the process were applied. In accordance with the present invention, biophysical studies were carried out to understand the conformational changes, e.g., folding/unfolding properties of rhAHF in detail, with specific experimental approaches to investigate the existence of intermediate structures and their role in aggregation.

The interest in using liposomes as an AHF formulation excipient is three-fold. (1) Liposomes have previously been shown to stabilize protein against aggregation and act as molecular chaperones, altering the protein-folding pathway (Yoshimoto et al., *Biotechnol. Prog.* 15:480-7 (1999); Balasubramanian et al., *Pharm. Res.* 17:344-50 (2000), which are hereby incorporated by reference in their entirety). (2) Surface modified liposomes have been shown to alter the circulation time of protein therapeutics, making them attractive delivery vehicles for biotechnology-derived products (Kanaoka et al., *Int. J. Pharm.* 188:165-72 (1999); Woodle, *Chem Phys Lipids* 64:249-62 (1993), which are hereby incorporated by reference in their entirety). It has been documented that the AHF binds strongly to PS containing phospholipids (Gilbert et al., *J. Biol. Chem.* 267:15861-8 (1992); Gilbert et al., *Biochemistry* 32; 9577-9585 (1993), which are hereby incorporated by reference in their entirety) in vivo. In the present invention, the interaction of the protein with PS containing liposomes was examined to develop alterations in the protein-folding pathway and such alterations were exploited in the development of the delivery vehicle of the present invention. (3) Liposomes were used to shield the epitope regions, such as C2, to reduce immune response and antigenicity by lipid binding.

In accordance with the present invention, liposomes were used as an excipient to stabilize the AHF protein against the physical instability. Circular Dichroism ("CD") and fluorescence spectroscopy was used to study the temperature dependent folding/unfolding characteristics of the protein in the presence and absence of liposomes. ANS (1,8 anilininaphthalene sulfonate), a fluorescent probe that partitions into hydrophobic domains, was used to detect exposure of the AHF hydrophobic domains. The unfolding of the protein was associated with the exposure of hydrophobic domains as observed by ANS fluorescence. In the presence of 10% ethanol, exposure of hydrophobic domains was possible with structures closer to native state. Through equilibrium refolding studies it was found that the thermally denatured protein in the presence of liposomes follows a different folding pathway and may be due to the interaction of the liposomes with the AHF protein, possibly resulting in the formulation of a complex. The ramification of the present observation is that, this protein-liposome complex can be exploited as a delivery vehicle, not only to improve stability of factor VIII but also to prolong its circulation time in vivo.

In this invention, a liposome-containing AHF formulation has been developed to provide stability, improve the circulation time of the protein, and reduce immune responses, thus overcoming the problems associated with present clinical formulations.

Thus, an important aspect of this invention is the lipid-AHF protein complex based delivery vehicle. Optionally, this lipid-protein association can be coated with molecules such as Poly Ethylene Glycol (PEG) to provide stealth properties to the delivery vehicle.

The present invention enables the encapsulation of above about 3% of the protein, preferably above about 25% (+/− about 3%) of the AHF protein. The present invention enables the association of above about 0.5%, preferably above about 3%, more preferably above about 25%, and most preferably above about 75% of the AHF protein with a stabilizer.

EXAMPLES

The invention will be illustrated in greater detail by the following specific examples. It is understood that these examples are given by way of illustration and are not meant to limit the disclosure or the claims to follow.

The following include experimental procedures used in the examples of the present invention.

Example 1

Experimental Materials

Hen egg-white lysozyme was purchased from Sigma (St. Louis, Mo.) as a crystallized dialyzed and lyophilized powder (Batch No: 57M7045). Spectroscopy grade solvents were purchased from Pharmaco, Inc. (Brookfield, Conn.), and used without further purification. ANS (1-anilino-8-naphthalene sulfonate), a probe of hydrophobic domains (Purohit et al., *Biochemistry* 36:12355-123633 (1998); Balasubramanian et al., *Molec. Pharmacol.* 53:926-932 (1998); Aloj et al., *Arch. Biochem. Biophys.* 155:478-479 (1973), which are hereby incorporated by reference in their entirety), was purchased from Molecular Probes, Inc. (Eugene, Oreg.). The ethanol-water mixtures of the following examples were prepared by mixing appropriate volumes of ethanol and water as described in US Pharmacopia.

Example 2

Liposomal Preparation and Protein Encapsulation

10 μmol/ml of DMPC (dimyristoyl phosphatidyl choline) was dissolved in chloroform and the solvent was evaporated using a rotary evaporator to form a thin film in a round bottomed flask. MLVs ("multi-lamellar vesicles") encapsulating the protein were formed by dispersing the lipid film in 20% ethanol-water mixture containing 2mg/ml of lysozyme with gentle swirling at 30° C., 40° C., and 70° C. The solvent was removed using nitrogen and replaced by distilled water. This procedure was used to encapsulate the protein in its native-like structure or intermediate structure; but for the encapsulation of native states, the lipid film and the protein was dispersed in water at 30° C.

Protein encapsulation was performed in accordance with the above procedure using the following solutions:

| | |
|---|---|
| Solution A | 200 μl ethanol in 800 μl water = approximately 20% ethanol |
| Solution B | 300 μl ethanol in 700 μl water = approximately 30% ethanol |
| Solution C | 500 μl ethanol in 500 μl water = approximately 50% ethanol |
| Solution D | 600 μl ethanol in 400 μl water = approximately 60% ethanol |
| Solution E | 700 μl ethanol in 300 μl water = approximately 70% ethanol |

Example 3

Circular Dichroism Experiments

CD spectra were acquired on a JASCO J715 spectropolarimeter calibrated with d10 camphor sulfonic acid. Temperature scans were acquired using a Peltier 300 RTS unit and the melting profiles were generated using software provided by the manufacturer. The spectra were acquired at heating rates of 60° C./hr and 120° C./hr: the data presented here are for 60° C./hr. For all the samples, a 10 mm cuvette was used to acquire the data. Samples were scanned in the range of from 260 nm to 200 nm for secondary structural analysis, and the protein concentration used was 20 g/ml. For near UV CD studies, the spectra were acquired in the range of from 360 nm to 270 nm, and the protein concentration used was 0.66 mg/ml. CD spectra of the protein were corrected by subtracting the spectrum of the solvent alone, and multiple scans were acquired and averaged to improve signal quality.

The refolding experiments were performed by dilution of the 70% or 30% (v/v) ethanol-water sample 10-fold with water to give 7% or 3% solvent respectively. The spectra were normalized for the effect of dilution by increasing the path length accordingly. For example, for 70% ethanol-water solution, the path length used was 1 mm and for 7% solution the path length of the cuvette was increased to 10 mm to account for the dilution. In addition, the contribution of the dilution effects were analyzed as follows; (1) the mean residue ellipticity was computed to normalize for the concentration of the protein and the path length of the quartz cuvette used; (2) the shape of the spectra also was analyzed as the shape does not vary with dilution.

Example 4

Fluorescence Studies

Fluorescence spectra were acquired on an SLM 8000C spectrofluorometer (Urbana, Ill.). Emission spectra were acquired over the range of from 400 nm to 550 nm, using a slit width of 4 nm on the excitation and emission paths. The excitation monochromator was set at 380 nm and the emission was monitored at 482 nm. Correction for the inner filter effect was performed by appropriate procedures (Lakowicz, *Principles of Fluorescence Spectroscopy*, Plenum Press, New York, (1986), which is hereby incorporated by reference in its entirety). Samples were maintained at the desired temperature using a water bath (Neslab RTE 110, NESLAB Instruments. Inc., Newington, N.H.). Spectra were corrected through the use of an internal reference and further processed using software provided by the manufacturer.

Example 5

Equilibrium Folding Analysis

A two-state unfolding model was applied to analyze the equilibrium unfolding data. Each unfolding curve was normalized to the apparent fraction of the unfolded form ($F_{app}$), using the relationship:

$$F_{app}=(Y_{obs}-Y_{nat})/(Y_{unf}-Y_{nat})$$

where $Y_{obs}$ is the ellipticity (at 220 nm or 290 nm) at a given temperature, and $Y_{unf}$ and $Y_{nat}$ are the spectral values for unfolded and native structures, respectively. $Y_{unf}$ and $Y_{nat}$ are obtained by performing a linear regression analysis of the spectrum plateau region at high and low temperatures, respectively.

Example 6

ANS Binding Studies

ANS (1-anilino-8-naphthalene sulfonate) was dissolved at 1 mg/ml containing 2% ethanol, and a small volume was added to a solution of 10 M of lysozyme in water, to give a final probe concentration of 0.3 M. The initial fluorescence intensity of the probe was normalized to account for the general solvent effects of ethanol on fluorescence measurements.

Example 7

Biological Activity Assay

The activity of lysozyme was determined by measuring the catalytic activity of the protein as described earlier (Rariy et al., *Biotechnol. Bioeng.* 62:704-710 (1986); Rariy et al., *Proc. Natl. Acad. Sci. USA* 94:13520-13523 (1997), which are hereby incorporated by reference in their entirety). The refolded protein was diluted 20 times into an assay mixture containing a prefiltered cell suspension of 0.16 mg/ml of M.lysodeikticus and the change in absorbance at 450 nm was monitored for the bacteriolytic activity of the protein. Control experiments were performed for ethanol concentrations of from 0% to 100% and the resultant data indicated that the presence of ethanol did not contribute to the activity measurement.

Example 8

Separation of Free Protein from Liposome Bound Protein

The liposome bound protein was separated from free protein by dextran centrifugation gradient. 0.5 ml of the liposome bound protein was mixed with 1 ml of 20% w/v of dextran and 3 ml of 10% w/v of dextran was layered over the above solution. Then 0.5 ml of water layered on the top of the above solution. The gradient was centrifuged for 35 min at 45K RPM using Beckman SW50.1 rotor.

Example 9

Molecular Topology of Liposomal Protein

The surface of the protein exposed to bulk aqueous compartment was investigated using acrylamide quenching and trypsin digestion. The fluorescence quenching by acrylamide is carried out to determine the accessibility of the protein surface to collisional quencher and would provide information on the location of the protein in liposomes.

Example 10

Thermal Denaturation Studies

Thermal stress is very often used as a denaturant to unfold protein (Morozova et al., *Biophys. Chem.*, 41:185-191 (1991), which is hereby incorporated by reference in its entirety) and to investigate the formation of intermediate structure(s). As unfolding of lysozyme in water follows a two-state model without the formation of intermediate(s) (Ikeguchi et al., *Biochemistry* 25:6965-6972 (1986), which is hereby incorporated by reference in its entirety), ethanol was used in combination with thermal stress to generate intermediate structure(s).

Example 11

Secondary Structure and Unfolding

Far-UV CD spectra were acquired for lysozyme at different temperatures in various ethanol-water mixtures and a melting curve was generated using ellipticity values at 220 nm (FIG. 1A). In water, lysozyme undergoes thermal unfolding with a Tm of 74° C. The addition of ethanol (5% to 60% v/v) resulted in the reduction of the Tm to 72.5° C. The superposition test was applied for the melting curves obtained for lysozyme in the presence and in the absence of ethanol, to determine the effect of ethanol on unfolding cooperativity (Luo et al., *Proc. Natl. Acad. Sci. USA* 96:11283-11287 (1999), which is hereby incorporated by reference in its entirety). In water, the unfolding transition curve was broader compared to that observed in ethanol-water mixtures, suggesting a weaker cooperative transition for lysozyme in water. At 40° C., in the presence of ethanol, the protein retained several of its native-like secondary structure features.

Example 12

Tertiary Structure and Unfolding

The melting of lysozyme in various ethanol-water mixtures was studied by near-UV CD spectra and a melting curve was generated by plotting ellipticity values at 290 nm as a function of temperature (FIG. 1B). The Tm decreased as the ethanol concentration was increased. In water, the melting curve obtained for tertiary structural change overlaps with that observed for secondary structure, with a Tm around 74° C. This observation is consistent with previously reported results (Knubovets et al., *Proc. Natl. Acad. Sci. USA*, 96:1262-1267 (1999), which is hereby incorporated by reference in its entirety) suggesting that intermediate(s) are not formed during unfolding of lysozyme in water. Further, unlike secondary structural changes, the unfolding of tertiary structure in water was more cooperative, similar to that observed in ethanol-water mixtures. However, it is interesting to note that the folding characteristics of secondary and tertiary structures measured for lysozyme in ethanol-water mixtures did not overlap (FIGS. 1A and 1B). For instance, at lower ethanol concentrations (20% v/v), the midpoint of transition for the near UV CD spectrum occurred around 68.75° C. while in contrast, the transition detected by far UV CD was higher, approximately 72.5° C. In the temperature range between 68.75° C. and 72.5° C., the protein existed in a conformation where it lost its tertiary structure but has intact secondary structure. This molecular property is a characteristic of intermediate state. However, at 40° C., the conformation of the protein is highly comparable to that of the native state. The cooling curve acquired for the secondary and tertiary structural changes were reversible. Similarly, the near UV CD spectra of the unfolding of the lysozyme at higher ethanol concentrations (60% v/v) showed that the protein melted around 60° C., whereas the Tm determined by far UV CD spectra was 72.5° C. Thus, the midpoint of the melting curve for secondary and tertiary structure did not overlap, indicating the existence of intermediate structure(s).

Example 13

Effects of Thermal Denaturation on the Exposure of Hydrophobic Domains

Figure 2:
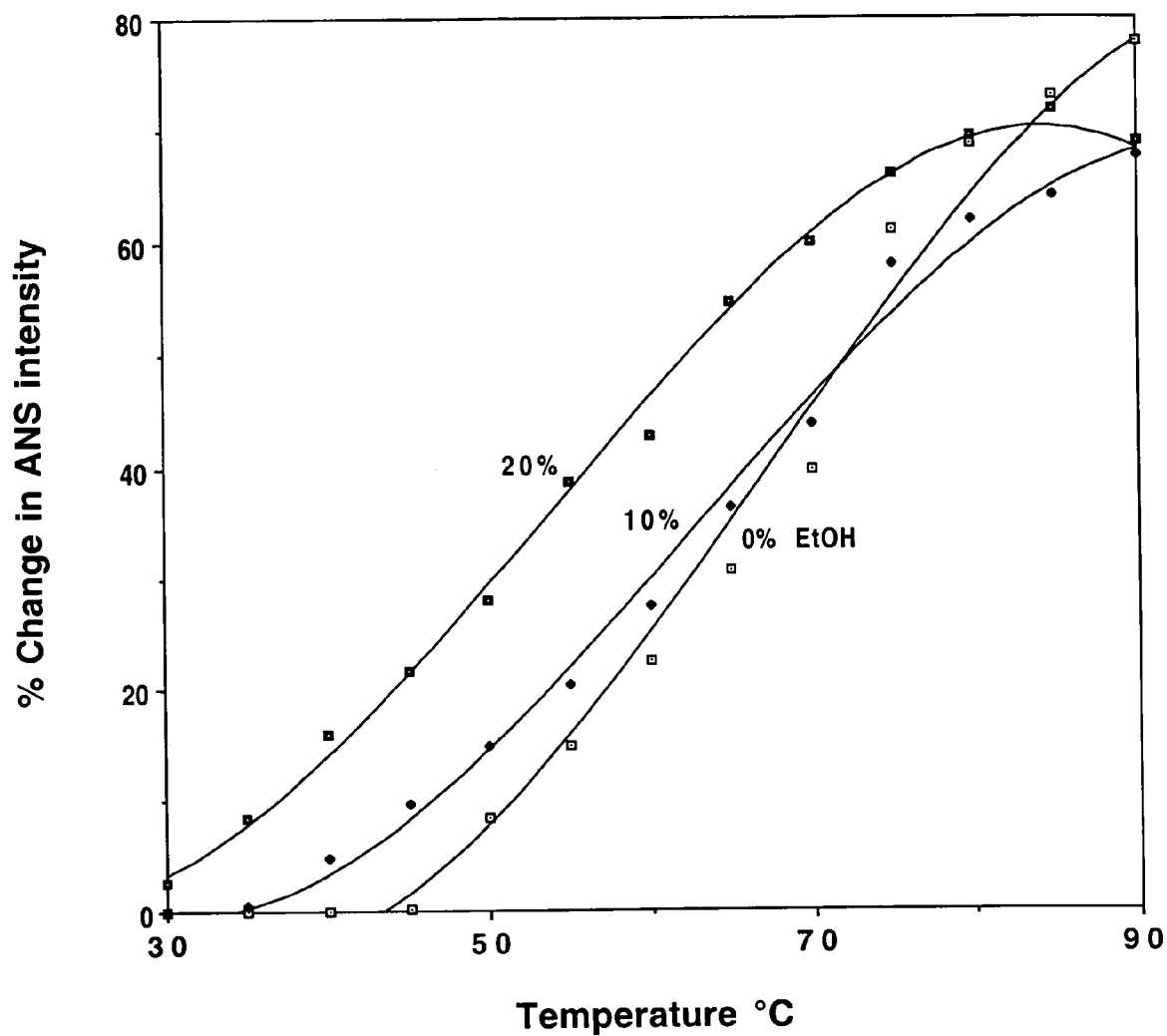
FIG. 2 is a plot of the % change in the ANS complex formation as a function of temperature.

Unfolding of the protein often results in the exposure of hydrophobic domains and the binding of fluorescence probes such as 1,8 anilinonaphthalene sulfonate (ANS) have been used effectively to investigate the surface properties of the unfolding proteins (Aloj et al., *Arch. Biochem. Biophys.* 155: 478-479 (1973); Balasubramanian et al., *Mol. Pharmacol.* 53:926-932 (1998); Purohit et al., *Biochemistry*, 36:12355-12363 (1998), which are hereby incorporated by reference in their entirety). The fluorescence intensity of the lysozyme-ANS complex was monitored in ethanol water mixtures as a function of temperature (FIG. 2). In water, the fluorescence intensity was unchanged in the temperature range of 25° C. to 50° C. while an increase in intensity was observed in the same temperature range for the lysozyme-ANS complex in 10% and 20% v/v ethanol-water mixtures. The data suggests that the exposure of hydrophobic domains occurs at lower temperatures in ethanol-water mixtures compared to that observed in water, possibly due to clustering of solvent molecules around the hydrophobic amino acids. In this temperature range, the conformation of the protein is comparable to the native state and does not indicate the formation of intermediate states. In order to account for the contribution of solvent enhanced fluorescence and weak binding of the probe to the native state, the initial fluorescence intensity of the probe was normalized and the temperature dependent effects were calculated as % change rather than absolute fluorescence intensity.

Example 14

Interaction of Ethanol-Induced Conformational States with Liposomes

When the protein is subjected to thermal stress in ethanol-water mixtures, the unfolding of the protein generates intermediate structures with exposed hydrophobic domains. This molecular characteristic is suitable for the liposomal encapsulation. In order to test this hypothesis we carried out the encapsulation of the protein in the presence of 20% ethanol-water mixtures at 40° C. at which the protein exists in a conformation where it exposes hydrophobic domains but does not have any properties of the conventional intermediate structures, whereas at 70° C., the protein displays the properties of an intermediate state. The solvent was removed by a nitrogen stream or by dialysis. It is appropriate to mention here that solvent removal resulted in the refolding of the protein as inferred from the equilibrium refolding experiments. Several control experiments including the encapsulation of the native state, i.e., protein in water (in the absence of ethanol) at 40° C., was also carried out (Table 1). Additional experiments, including the encapsulation of the protein in water (in the presence and in the absence of ethanol) at 70° C., were also carried out (Table 1). The free protein is separated from liposome bound protein by dextran centrifugation gradient and the % encapsulation of the protein was estimated by BCA protein quantitation, UV absorbance and fluorescence assay. It is clear from the data that the intermediate structure mediated encapsulation into the liposomes yielded higher encapsulation efficiency compared to the native state of the protein.

TABLE 1

| Sample | % Protein Associated, (n = 12) ± SE (mean) |
|---|---|
| Native state, pH 7.4, 30° C. and 40° C. | 37 ± 8.85% (at 40° C., n = 10) |
| Conformational state with exposed hydrophobic domain with high tertiary structure (pH 7.4, 10-20% ethanol, 40° C.) | 59 ± 18.33% (n = 12) |
| Conventional Intermediate (at 70° C., 20% ethanol) and Unfolded State (70° C. in the absence of ethanol) | 47 ± 15.94% and 43 ± 9.61% (n = 12) |

Example 15

Additional Molecular Topology Studies of Liposomal Protein

This example further exemplifies additional molecular topology studies of liposomal protein studies, conducted via use of materials prepared by and/or by experimental procedures described in Example 8 and other examples above. As in Example 8, the present example describes use of circular dichroism (cd) experiments to investigate secondary and tertiary protein structural changes.

Example 16

Circular Dichroism (CD) Experiments

In each of the following experimental sections, CD spectra were acquired on a JASCO J715 spectropolarimeter calibrated with $d_{10}$-camphor sulfonic acid. Temperature scans were acquired using a Peltier 300 RTS unit and the unfolding profiles generated using software provided by the manufacturer.

The temperature dependent changes in secondary and tertiary (FIGS. 4A and 4B) structure of lysozyme in ethanol-water mixtures, are compared by plotting ellipticity at 220 nm and 290 nm as a function of temperature. The melting profiles were collected over the temperature range of from 25° C. to 95° C. with a heating rate of 60° C./hr at every 0.5° C. intervals. Each data point is an average of three experiments. $F_{app}$, the fraction of protein in the unfolded state, is calculated as described above in the experimental procedures.

For secondary structure, the path length of the cuvette used was 10 mm, and the concentration of protein was 20 μg/ml. For tertiary structural measurements, the path length of the cuvette used was 10 mm, and the concentration of protein was 0.66 mg/ml. 20 μg/ml. For tertiary structures used in these experiments, a 10 mm quartz cuvette was used to acquire the data. Samples were scanned over the range of 360-270 nm and the protein concentration was typically ~660 μg/ml. Presence of ethanol resulted in the formation of intermediate structures in the unfolding pathway of the protein, in contrast, an aqueous environment did not promote any such intermediate structures. For example, in 20% (v/v) ethanol-PBS mixture (pH=7.4), the Tm for the secondary and tertiary structures were 61.75° C. and 58° C. In phosphate buffer (pH=7.0) the Tm were ~73° C. and 72.25° C. respectively.

Example 17

Secondary and Tertiary Structural Changes (FIGS. 4A and 4B) Secondary Structure and Unfolding Far-UV CD spectra were acquired for lysozyme at different temperatures in the indicated ethanol-water or ethanol-buffer mixtures (pH=7.0 or 7.4) and unfolding curves were generated using ellipticity values at 220 nm (FIG. 4(a)). The spectra were acquired at a heating rate of 60° C./hr. For all samples, a 10 mm quartz cuvette was used to acquire the data. Samples were scanned over the range of 260-200 nm and the protein concentration was typically ~20 μg/ml.

Example 18

Tertiary Structure and Unfolding

Near-UV CD spectra were acquired for lysozyme at different temperatures in the indicated ethanol-water or ethanol-buffer mixtures (pH=7.0 or 7.4) and unfolding curves were generated using ellipticity values at 290 nm (FIG. 4(b)). The spectra were acquired at a heating rate of 60° C./hr.

For all samples used in these experiments, a 10 mm quartz cuvette was used to acquire the data. Samples were scanned over the range of 360-270 nm and the protein concentration was typically ~660 μg/ml. Presence of ethanol resulted in the formation of intermediate structures in the unfolding pathway of the protein, in contrast, an aqueous environment did not promote any such intermediate structures.

For example, in 20% (v/v) ethanol-PBS mixture (pH=7.4), the Tm for the secondary and tertiary structures were 61.75° C. and 58° C. In phosphate buffer (pH=7.0) the Tm were ~73° C. and 72.25° C. respectively. The aforementioned differences in Tm between the secondary and tertiary structures clearly indicate the presence of intermediate structures.

Significantly, the grade of ethanol (i.e., reagent, solvent, absolute, commercial grade, etc.) appears to influence the experimental conditions under which such intermediate structures are generated. Hence, specific temperature or temperature ranges in combination with solvents, such as ethanol are useful to promote protein conformational structures, which include secondary, intermediate and/or tertiary protein structures, with exposed hydrophobic domains. Such intermediate structures are useful to engineer a hydrophobic interaction with liposomes to increase encapsulation efficiency.

In light of above (i.e., with regard to secondary structure and unfolding), the melting profile and transition temperature (Tm) measured by both secondary and tertiary structural changes in proteins, such as lysozymes, studied in the present invention, were sensitive to different and/or changes in experimental conditions. Such experimental conditions include changes in pH, components, buffer solutions, solvent grades and protein concentrations (FIGS. 4A and 4B). In particular, it was also observed that the Tm changed from one lysozyme batch to another based upon such changes in experimental conditions (i.e., three different lysozyme batches were tested under different experimental conditions).

In particular, these experiments determined that use of different experimental conditions based upon the different types of chemical and/or physical perturbants significantly affected the different protein conformation states and/or characteristics experimentally observed. In particular, it was determined that protein complexation with different chemical perturbants, stabilizers, excipients, solutions, etc. occurs under different experimental conditions, achieved by use of different buffer solutions at a different pH or within a pH range, use of chemical or reagent grade solvents (i.e., of ethanol or other chemical solutions) as commercially available and at different protein concentrations as indicated therein.

In all cases, secondary structural changes in tested proteins, such as lysozymes, as a function of thermal stress in ethanol-water mixtures were found to retain substantial residual secondary structural characteristics, found to be less cooperative compared to the tertiary structural changes, leading instead to the generation of intermediate structures characterized as a hybrid structure having secondary and tertiary structural characteristics. For example, at 70° C., a tested protein lost all of its tertiary structural characteristic change, whereas secondary protein or substantially residual secondary protein structure(s), characteristics, or features were observed. At 40° C., the tested protein retained both secondary and tertiary structural features.

As previously indicated, such a protein may be stabilized in its different corresponding protein structural or conformational stated under appropriate reaction conditions. For example, a stabilized secondary or substantially secondary protein structure(s) form with exposed hydrophobic domains may be formed by contact with a 20% ethanol-water mixture or 20% ethanol-phosphate buffered saline solution at pH range from about 7.0 to about 7.4 at temperature range from about 70° C. to about 74° C., binding a stabilizer to the exposed hydrophobic domains, which may include at least partially reversing the alteration to associate at least a portion of the protein with the stabilizer. Further such a protein may be stabilized in its secondary-tertiary hybrid intermediate protein structure(s) with exposed hydrophobic domains by contacting with a 20% ethanol-water mixture or 20% ethanol-phosphate buffered saline solution at pH range from about 7.0 to about 7.4 at temperature range from about 58° C. to about 62° C., binding a stabilizer to the exposed hydrophobic domains, which may include at least partially reversing the alteration to associate at least a portion of the protein with the stabilizer.

Figure 3:
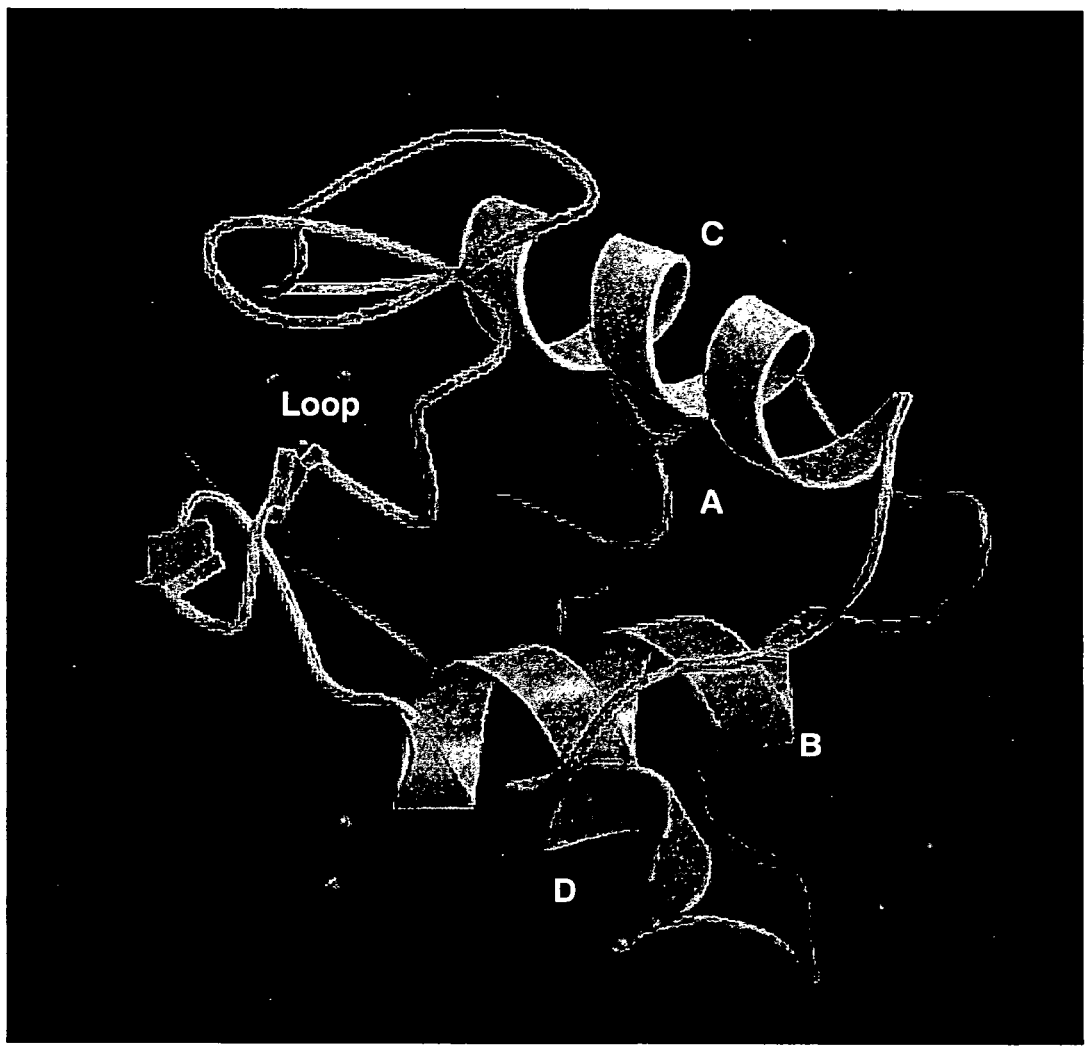
FIG. 3 is a ribbon diagram of the three dimensional structure of lysozyme.

Ethanol mediated stabilization of helical hydrophobic core structure, which include the A, B, and D helices may be responsible for the observation of residual secondary structure (FIG. 3). Overall, at 70° C., lysozyme exists in intermediate structure and displays properties of that intermediate structure state in 20% ethanol-water mixtures.

Example 19

Temperature Dependence of Secondary and Tertiary Structure of Lysozyme in Various Ethanol-Water Mixtures The temperature dependent changes in secondary (FIG. 1A) and tertiary (FIG. 1B) structure of lysozyme in ethanol-water mixtures, are compared by plotting ellipticity at 220 nm and 268 nm as a function of temperature. The melting profiles were collected over the temperature range of from 25° C. to 95° C. with a heating rate of 60° C./hr at every 0.5° C. intervals. Each data point is an average of three experiments. $F_{app}$, the fraction of protein in the unfolded state, is calculated as described above in the experimental procedures. For secondary structure, the path length of the cuvette used was 10 mm, and the concentration of protein was 20 µg/ml. For tertiary structural measurements, the path length of the cuvette used was 10 mm, and the concentration of protein was 0.66 mg/ml.

Example 20

Exposure of Hydrophobic Domains of Lysozyme in Ethanol-Water Mixtures Probed by ANS Complex Formation ANS was dissolved at high concentration in water and a small volume was added to a solution of 10 µM of lysozyme, to a final probe concentration of 0.3 µM. The samples were excited at 380 nm and the emission was monitored at 482 nm. Results are shown in FIG. 2. Each data point is an average of three experiments.

Example 21

Ribbon Diagram of the Three Dimensional Structure of Lysozyme

The hydrophobic core comprising four major helices are marked as A (5-15), B (25-36), C (88-101), and D (109-115), in FIG. 3.

Example 22

Secondary and Tertiary Structural Changes

The temperature dependent changes in secondary and tertiary (FIGS. 4A and 4B) structure of lysozyme in ethanol-water mixtures, are compared by plotting ellipticity at 220 nm and 290 nm as a function of temperature. The melting profiles were collected over the temperature range of from 25° C. to 95° C. with a heating rate of 60° C./hr at every 0.5° C. intervals. Each data point is an average of three experiments. $F_{app}$, the fraction of protein in the unfolded state, is calculated as described above in the experimental procedures.

Example 23

Experimental Materials rhAHF protein was provided by Baxter Health Care (Deerfield, Ill.), and was used without further purification. ANS (1-anilino-8 naphthalene sulfonate), a hydrophobic probe (Aloj et al., *Arch. Biochem. Biophysics* 155: 478-479 (1973); Purohit et al., *Biochemistry* 36:12355-63 (1997); Balasubramanian et al., *Mol Pharmacol* 53:926-32 (1998), which are hereby incorporated by reference in their entirety) was purchased from Molecular Probes, Inc. (Eugene, Oreg.). Lipids were obtained from Avanti polar lipids (Alabaster, Ala.), and used without purification.

Example 24

Preparation of Liposomes

In the procedure according to the conventional method: 0.30 mg/ml DMPC, 0.15 mg/ml bPS and 0.04 mg/ml DSPE-PEG dissolved in chloroform were taken in a round-bottomed flask and the solvent was removed using a rotary evaporator, depositing the lipid as a thin film along the walls of the flask. Multilamellar vesicles (MLV) encapsulating the protein were formed by dispersing the lipid film in the appropriate buffer (0.4 M NaCl and 50 Mm Tris) containing 0.5 mg/ml of the protein, with gentle swirling at room temperature.

Figure 14:
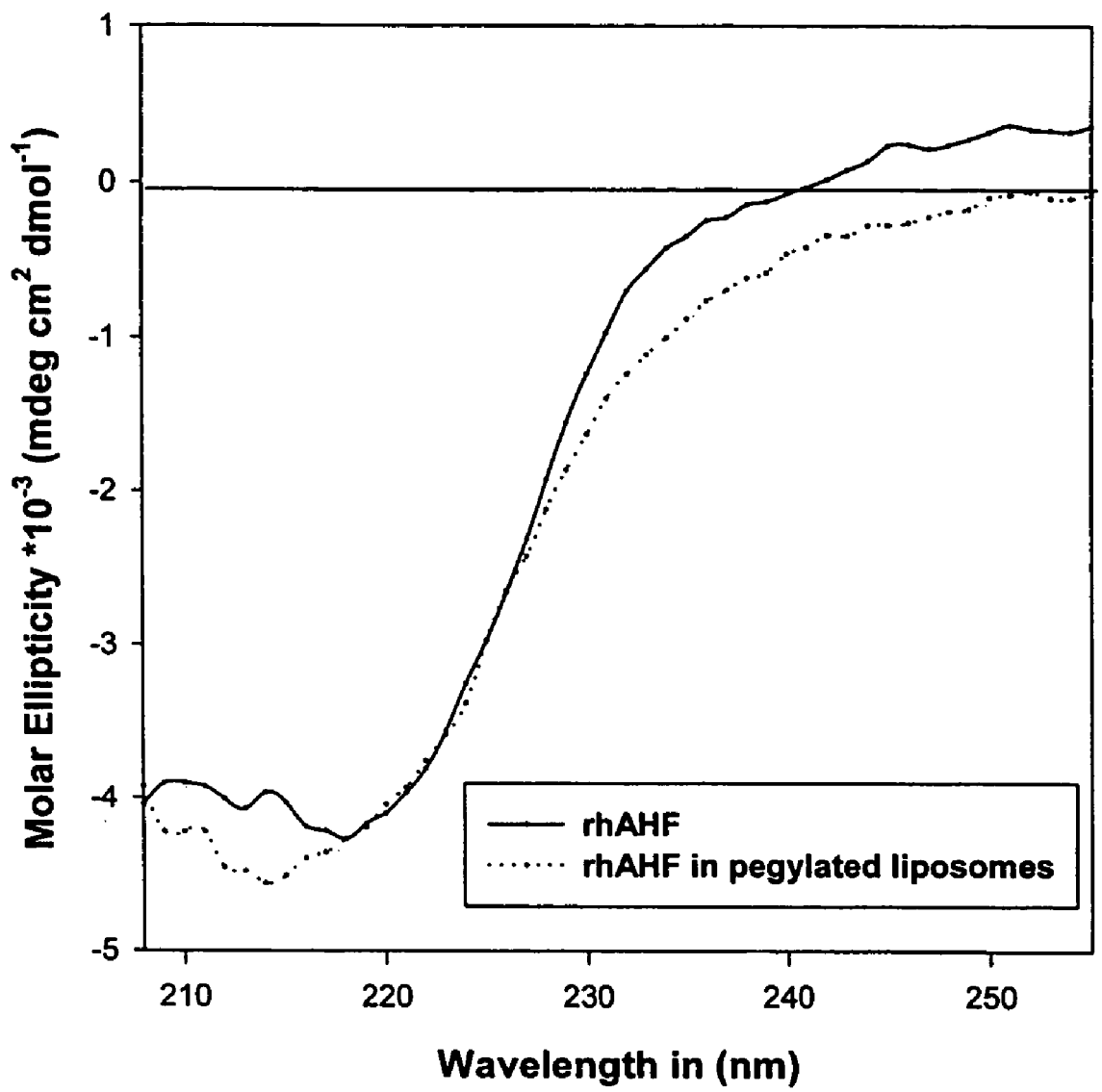
FIG. 14 is a graph showing the effect of liposomes on the secondary structure of rhAHF.

In the procedure according to the present method: 0.30 mg/ml DMPC, 0.15 mg/ml bPS and 0.04 mg/ml DSPE-PEG dissolved in chloroform were taken in a round-bottomed flask and the solvent was removed using a rotary evaporator, depositing the lipid as a thin film along the walls of the flask. Multilamellar vesicles (MLV) encapsulating the protein were formed by dispersing the lipid film in the appropriate buffer (0.4 M NaCl and 50 Mm Tris and ~10%v/v ethanol) containing 0.5 mg/ml of the protein, with gentle swirling at room temperature or at 37° C. The protein stock solution was prepared by adding 50 ml of 95% ethanol to 450 ml of the protein solution in the specified buffer. Ethanol was then removed using a liquid nitrogen flow at room temperature or at about 37° C. A graph of data generated from this example showing the effect of liposomes on the secondary structure of rhAHF: Far-UV CD spectra of rhAHF were acquired in the presence and absence of PEGylated liposomes composed of DMPC (dimyrsitolphosphatidyl choline), bPS (brain phosphatidylserine) and DSPE-PEG (distearoyl phosphatidyl ethanolamine-Polyethylene Glycol-2000) is shown in FIG. 14.

In the present invention, several preparation procedures were attempted to achieve the goals. 0.3 mg/ml DMPC, 0.15 mg/ml bPS, cholesterol dissolved in chloroform were taken in a round bottomed flask and the solvent was removed using a rotary evaporator, depositing the lipid as a thin film along the walls of the flask. The MLVs thus formed were filtered through a polycarbonate filter (0.22 µpm) to form SUVs below 200 nm. The liposomes encapsulating the protein were formed by mixing the liposomes in protein containing buffer and ethanol followed by gentle swirling at 37° C. or at higher temperatures to generate intermediate structures. The average diameter of the particles was 160 nm. The PEGylation of these particles was performed by adding DSPE-PEG.

Example 25

Circular Dichroism Experiments

CD spectra were acquired on a JASCO-715 spectropolarimeter calibrated with d10 camphor sulfonic acid. Samples were scanned in the range of from 205 nm to 255 nm for secondary structure analysis, and typically, the protein concentration used was about from 20 µg/ml to 22 µg/ml. For near-UV CD studies, spectra were acquired in the range of from 320 nm to 255 nm, using a 10 mm quartz cuvette, and the protein concentration used was about 0.5 mg/ml. CD spectra of the protein were corrected by subtracting the spectrum of the buffer baseline and multiple scans were acquired and averaged to improve signal quality. The CD spectra of samples containing liposomes may be distorted as a result of light scattering. The contribution due to light scattering was corrected as follows: (1) the ellipticity values at from 350 nm to 400 nm were monitored and used as a baseline that was subtracted from the scans; (2) multiple scans were acquired and averaged to improve the signal quality. The spectra thus obtained were invariant with the path length of the cuvette, dilution of the sample or position of the sample along the light path, indicating that the effect of scattering on the spectra was minimal.

Example 26

Fluorescence Studies

Fluorescence spectra were acquired on a SLM 8000C spectrofluorometer (Urbana, Ill.). The intensity of the emission spectra was monitored over the range of from 300 nm to 400 nm, using a slit width of 4 nm on the excitation and emission paths. The excitation monochromator was set at 280 nm and a 295 nm long pass filter was used to minimize scattering effects. The melting of the protein was followed by monitoring the decrease in the intensity of the emission at 330 nm over the temperature range of from 25° C. to 90° C. Samples were equilibrated at the desired temperature for approximately 3 to 4 minutes using a water bath (Neslab RTE 110).

Example 27

Equilibrium Folding Analysis

A two-state unfolding model was used to analyze the equilibrium unfolding data. To compare the transitions detected by several methods, each unfolding curve was normalized to the apparent fraction of the unfolded form ($F_{app}$), using the relationship:

$$F_{app}=(Y_{obs}-Y_{nat})/(Y_{unf}-Y_{nat})$$

where $Y_{obs}$ is the molar ellipiticity (at 215 nm or 295 nm) at a given temperature, and $Y_{unf}$ and $Y_{nat}$ are the spectral values for unfolded and native structures, respectively. $Y_{unf}$ and $Y_{nat}$ are obtained by taking the average of the spectrum plateau region at high and low temperatures, respectively.

Example 28

ANS Binding Studies

ANS (1-anilino-8-napthalene sulfonate) was dissolved in high concentration in the appropriate buffer and a small volume was added to a solution of 10 nM/ml rhAHF, to give a final probe concentration of 50 nM/ml. The excitation wavelength was 380 nm and the emission was monitored at 482 nm. Correction for the inner filter effect was performed by appropriate procedures as described above (Lakowicz, *Principles of Fluorescence Spectroscopy*, New York, Plenum Press (1986), which is hereby incorporated by reference in its entirety).

Example 29

Biological Activity Assay of rhAHF

RhAHF clotting activity was determined by a one-stage activated partial thromboplastin time (APTT) assay using micronized silica or $CaCl_2$ as an activator and AHF deficient plasma as the substrate. The APTT assay was performed using a COAG-A-MATE coagulation analyzer (Organon Teknika Corporation, Durham, N.C.). Briefly, rhAHF was added to AHF deficient plasma and the clotting time was monitored. The activity of the rhAHF was then obtained from a calibration curve constructed using the clotting times determined from various dilutions of a lyophilized reference concentrate of known activity.

Example 30

Thermal Denaturation Studies of rhAHF

Because the process of physical instability is related to protein unfolding at the molecular level, the immediate objective was to analyze the rhAHF protein unfolding in detail. Thermal denaturation studies have been commonly employed to understand the structural stability of protein therapeutics and to develop a pharmaceutically stable formulation (Tsai et al., *Pharm. Res.* 10:649-59 (1993); Balasubramanian et al., *Pharm. Res.* 17:344-50 (2000), which are hereby incorporated by reference in their entirety).

Example 31

Effect of Temperature of Secondary Structure

Figure 6A:
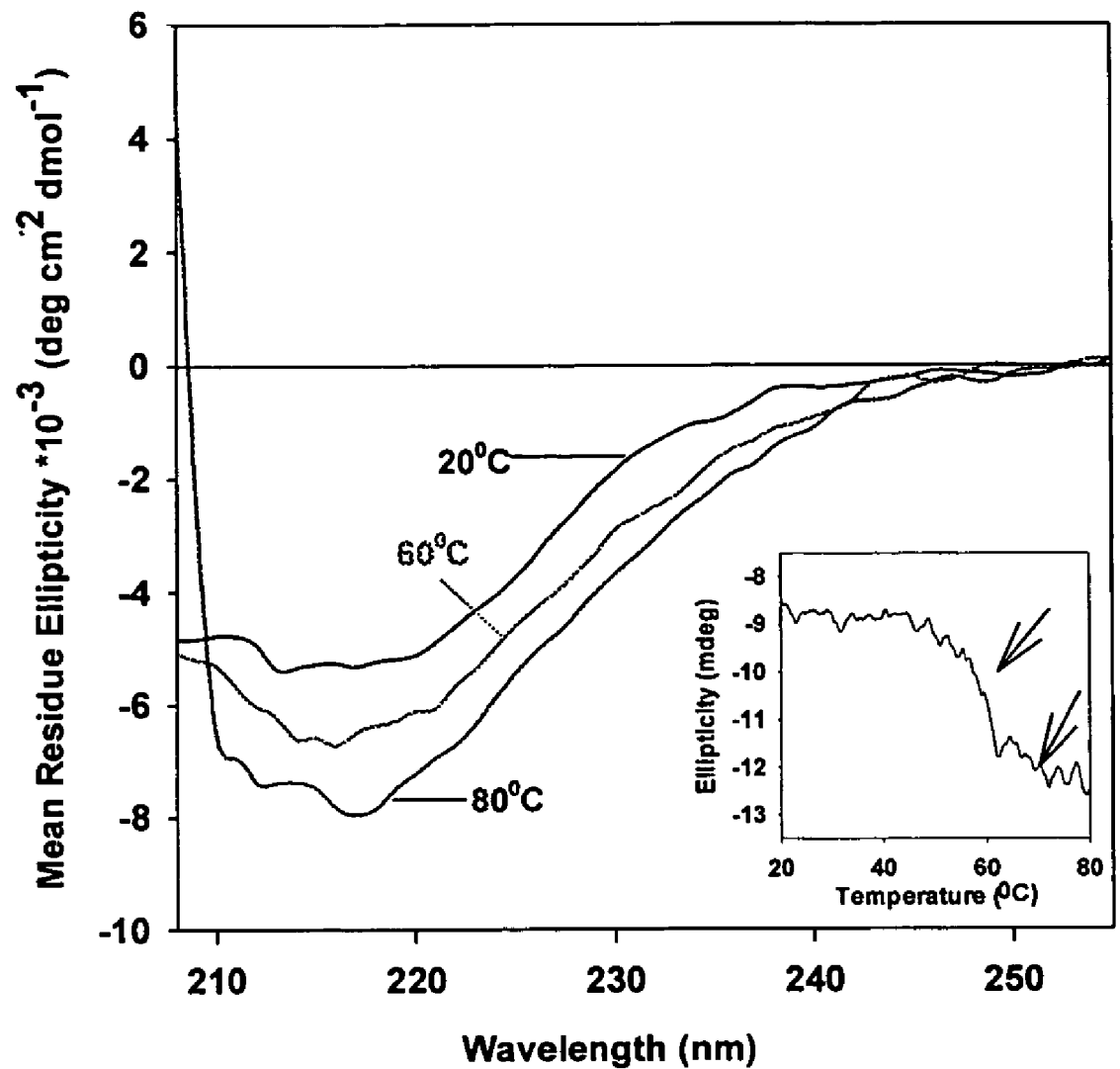
FIG. 6A is a graph of the far UV-CD spectra of the molar ellipticity of rhAHF in the appropriate buffer acquired between 20° C. and 90° C. over a wavelength range of from 208 nm to 255 nm.

Temperature induced changes in rhAHF secondary structure was studied by acquiring the far-UV CD spectra (255 nm to 205 nm, FIG. 6A). At 20° C., a broad negative band at 215 nm suggested that the protein existed predominantly in β-sheet conformation. This is in agreement with the structure, proposed based on homology modeling (Pan et al., *Nat. Struct. Biol.* 2:740-4 (1995), which is hereby incorporated by reference in its entirety). As the temperature is increased over the temperature range of from 20° C. to 50° C., there were no significant changes in the far-UV CD spectrum; indicating that the secondary structure of the protein was not altered. In the temperature range of from 50° C. to 65° C., the ellipticity at 215 nm increased progressively with increasing temperature suggesting an increase in the β-sheet conformation. At temperatures over 65° C., significant changes were observed in the spectral characteristics. The CD spectra had red-shifted by approximately 2 nm and appearance of a positive band in the range from 205 nm to 210 nm range suggested the formation of anti-parallel β-strands possibly leading to formation of aggregates eventually stabilized by intermolecular β-strands (Hilbich et al., *J. Mol. Biol.* 218:149-63 (1991); Hammarstrom et al., *J Biol Chem* 274: 32897-903 (1999), which are hereby incorporated by reference in their entirety). Thus the secondary structure appeared to undergo the following conformational transition:

parallel-β sheet - - - increased β-sheet content - - - anti-parallel β-sheets.

Far-UV spectral data was used to calculate the $F_{app}$, the apparent fraction in the unfolded form, according to the method described herein.

Example 32

Figure 6B:
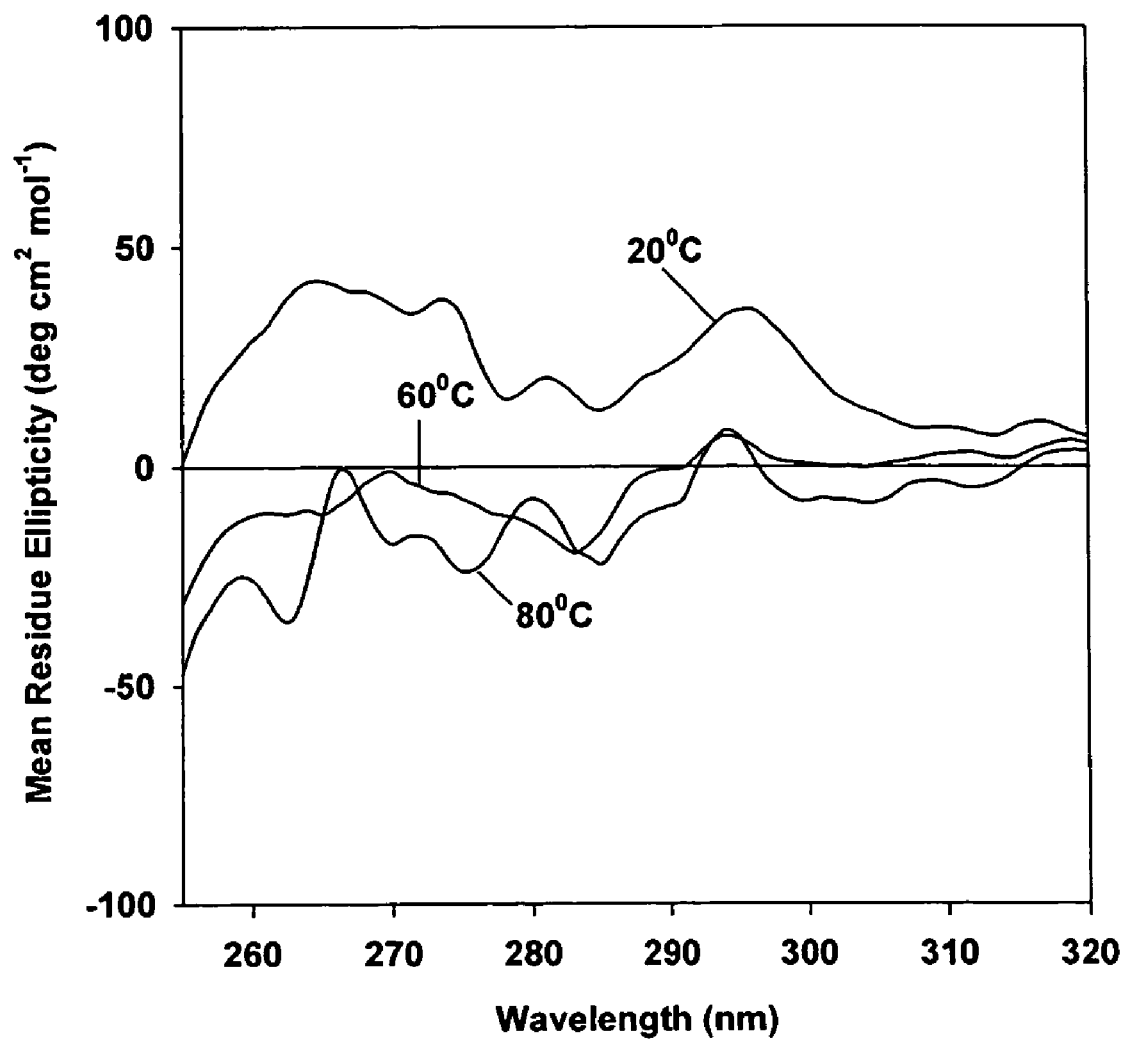
FIG. 6B is a graph of the near-UV CD spectra of the molar ellipticity of rhAHF in the appropriate buffer acquired between 20° C. and 80° C. over a wavelength range of from 255 nm to 320 nm.

Effect of Temperature on Tertiary and Secondary Structure and Evidence for the Existence of Structured Intermediates While the near-UV CD spectrum is indicative of the tertiary structure, the far-UV CD spectrum is indicative of the secondary structure. The temperature dependence of the near-UV CD spectrum over the wavelength range of from 255 nm to 320 nm was investigated (FIG. 6B). At 20° C., there were two positive peaks at about 295 nm and about 268 nm and as the temperature was increased, the intensity of the peaks decreased.

Figure 6C:
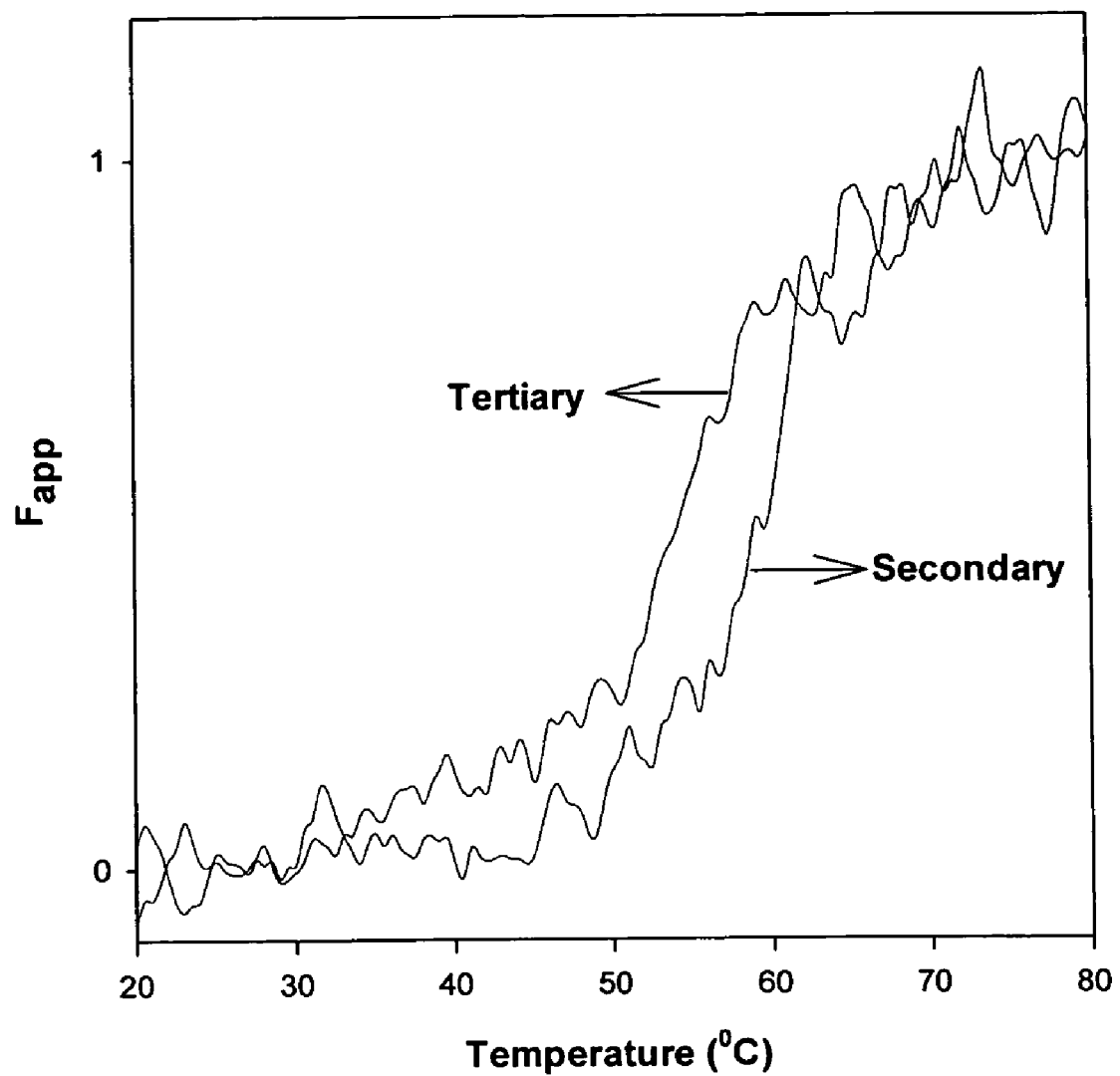
FIG. 6C is a graph of the ellipticity of rhAHF at 215 nm and 295 nm as a function of temperature.

The near-UV CD spectrum was used to calculate the temperature dependence of the unfolding of tertiary structure. With increase in temperature, ellipticity at 295 nm decreased and thus $F_{app}$ increased with midpoint of main transition occurring approximately in the range of from 50° C. to 52° C., (FIG. 6C). The temperature dependence of far-UV CD spectrum was monitored over the wavelength range of from 205 nm to 255 nm and the main transition detected by far-UV CD was considerably higher, approximately from 60° C. to 62° C., (FIG. 6C). Such a difference in the temperature at which tertiary and secondary structural changes occurred confirmed the existence of intermediate unfolded state(s)(Ptitsyn et al., *FEBS Lett* 262:20-24 (1990), which is hereby incorporated by reference in its entirety). While the multistage transition was apparent for the far-UV CD spectra, it was relatively less apparent for the near-UV CD spectra.

Figure 7:
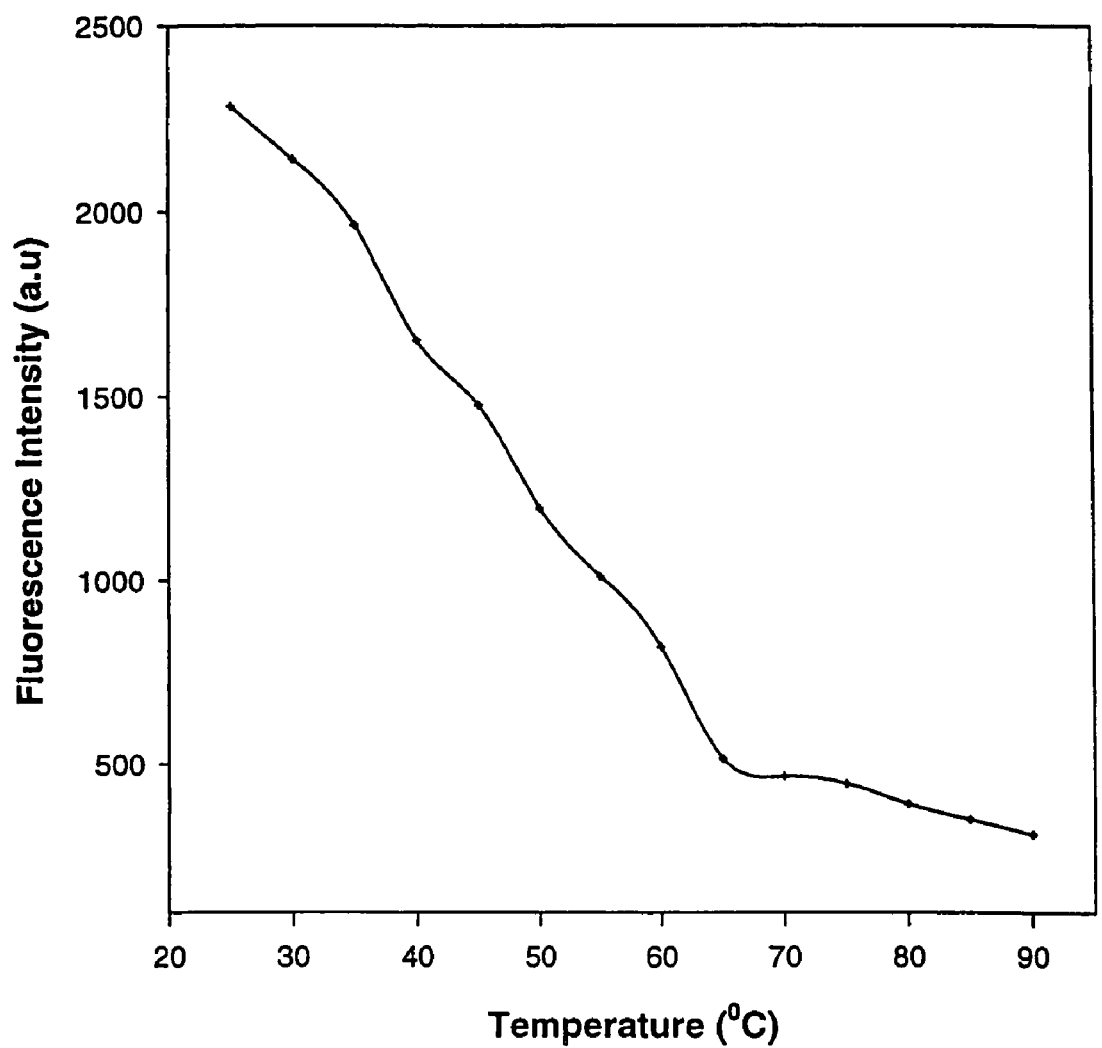
FIG. 7 is a graph of the temperature dependent changes in fluorescence intensity, measured in arbitrary units ("a.u."), of rhAHF.

Factor VIII is a multi-domain protein with several tryptophan residues and changes in Trp fluorescence may provide information on gross tertiary structural changes in the protein, spanning different domains. Fluorescence emission spectra of rhAHF were acquired over the temperature range of from 25° C. to 90° C. to detect changes in Trp fluorescence (FIG. 7). The data indicated multistage transitions and they did not overlap with the one observed by far-UV CD. Depending on % change in fluorescence intensity and near UV CD, several molecular species were identified (SI1, SI2, SI3). In the temperature range of 20-50° C., the structure was identified as SI1, possessing native like secondary and tertiary structural features with small conformational change in C2 domain resulting in exposure of hydrophobic domains. In the temperature range of 50-65° C., species SI2 was identified and may involve aggregates. The conformational state above 65° C., was designated as SI3 and may involve substantial aggregation as was clear from far UV CD studies that displayed spectral characteristics of intermolecular beta strands at higher temperatures. Control experiments were carried out with Tryptophan to evaluate the temperature dependent inactivation of the excited state and fluorescent intensity and the results indicate that in the temperature range of 20-50% the fluorescent intensity loss may be due to the inactivation and not involve substantial conformational change. This was further confirmed by Near UV CD studies.

Example 33

Effects of Thermal Denaturation of the Exposure of Hydrophobic Domains

Figure 8:
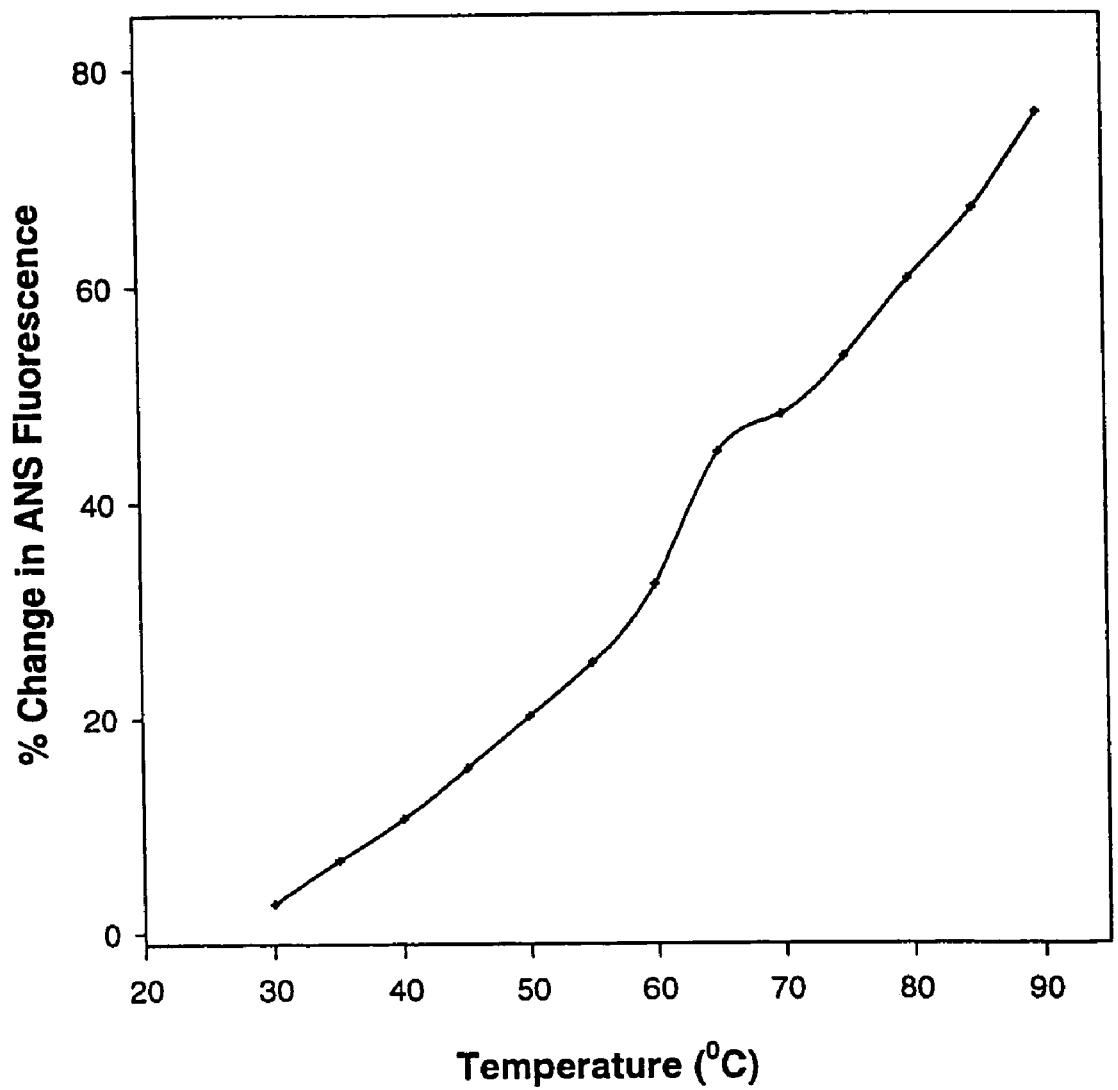
FIG. 8 is a graph of the % change in ANS fluorescence as a function of temperature.

To determine whether rhAHF forms intermediate structures with exposed hydrophobic domains during the unfolding process, the complexation of the protein with ANS, a probe of hydrophobic domains (Aloj et al., *Arch. Biochem. Biophysics* 155:478-479 (1973); Purohit et al., *Biochemistry* 36:12355-63 (1997); Balasubramanian et al., *Mol. Pharmacol.* 53:926-32 (1998), which are hereby incorporated by reference in their entirety) was monitored. The fluorescence intensity of protein bound ANS increased with increasing temperature (FIG. 8). Over the temperature range of from 25° C. to 45° C. the increase in ANS intensity was almost linear suggesting a progressive increase in the exposure of hydrophobic domains of $SI_1$. Over the temperature range of from 50° C. to 60° C., there was a substantial increase in intensity (about 40% increase in intensity at 65° C.), suggesting more exposure of hydrophobic domains and/or aggregate formation and may be associated with $SI_2$. The sharp increase in fluorescence of the protein-ANS complex in the temperature range of from 85° C. to 90° C. was an indication of protein aggregation, which occurred as a result of protein conformational changes that increased the exposure of hydrophobic domains and was consistent with the formation of $SI_3$.

Example 34

Conformational Changes in the Protein and its Implication

Figure 9:
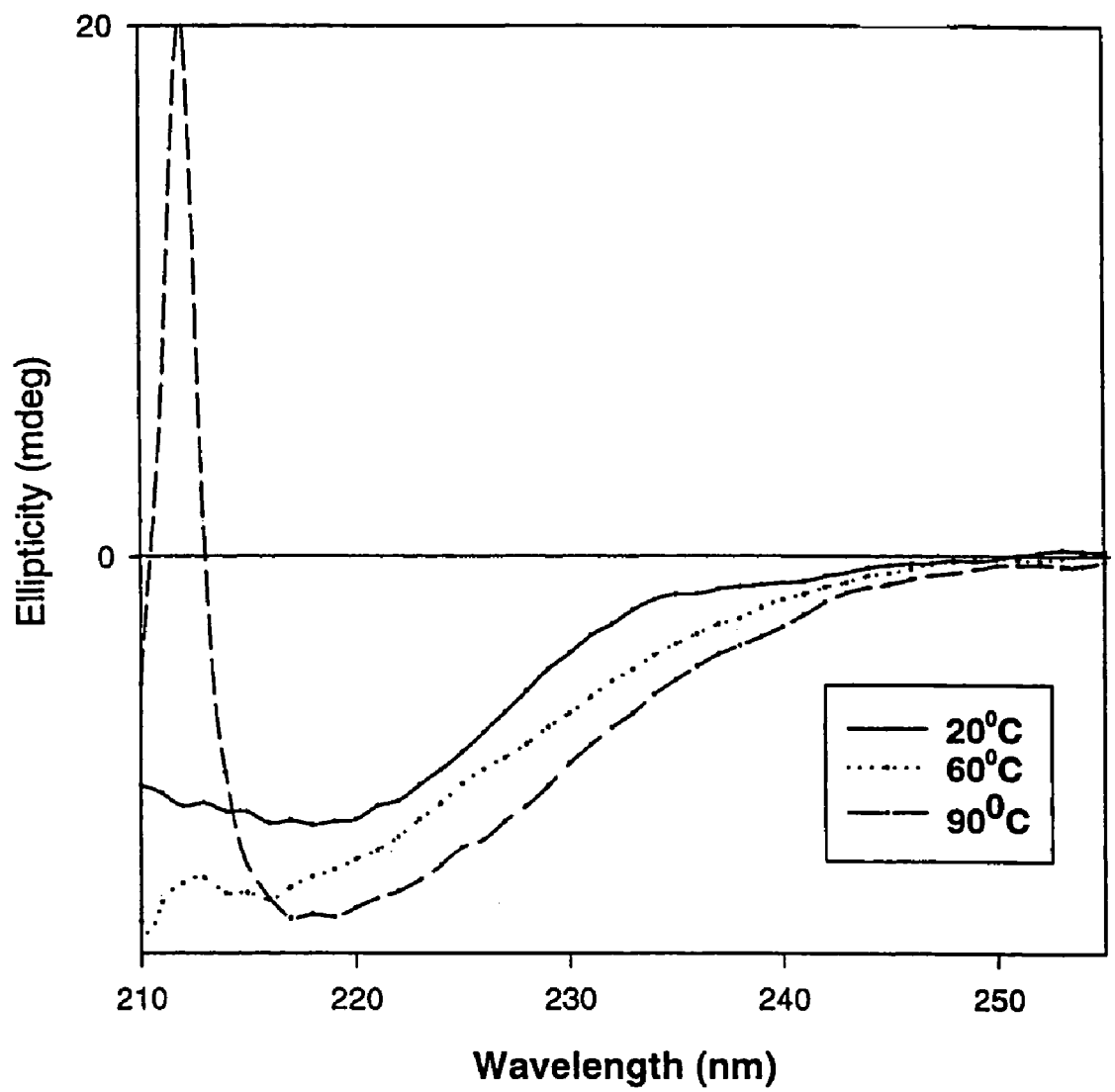
FIG. 9 is a graph of the ellipticity of rhAHF as a function of temperature.

In order to get an insight into the conformational changes in the protein that promotes the reported aggregation process and decrease in activity, the protein was incubated at various temperatures and the changes in the far-UV CD spectrum was monitored (FIG. 9). For the incubation study carried out at 90° C., formation of intermolecular β-strands was observed and the protein on annealing did not recover the native-like secondary structural features and the loss of native structural features was concomitant with loss of biological activity. It is speculated that the partially folded, structured intermediates ($SI_3$) with exposed hydrophobic domains promote aggregation and the aggregates are possibly stabilized by intermolecular β-strands resulting in loss of activity of the protein. This speculation is strongly reflected in the observed increase in ANS fluorescence at elevated temperatures. For the incubation studies at 37° C. and 47° C. that corresponded to formation of $SI_1$, no significant change in CD characteristics was observed, while at 60° C. that corresponded to formation of $SI_2$, an increase in the intensity of the band at 215 nm and a small blue shift was noted which is consistent with previous observations.

Example 35

Conformational Analysis of Liposomal rhAHF

Figure 10:
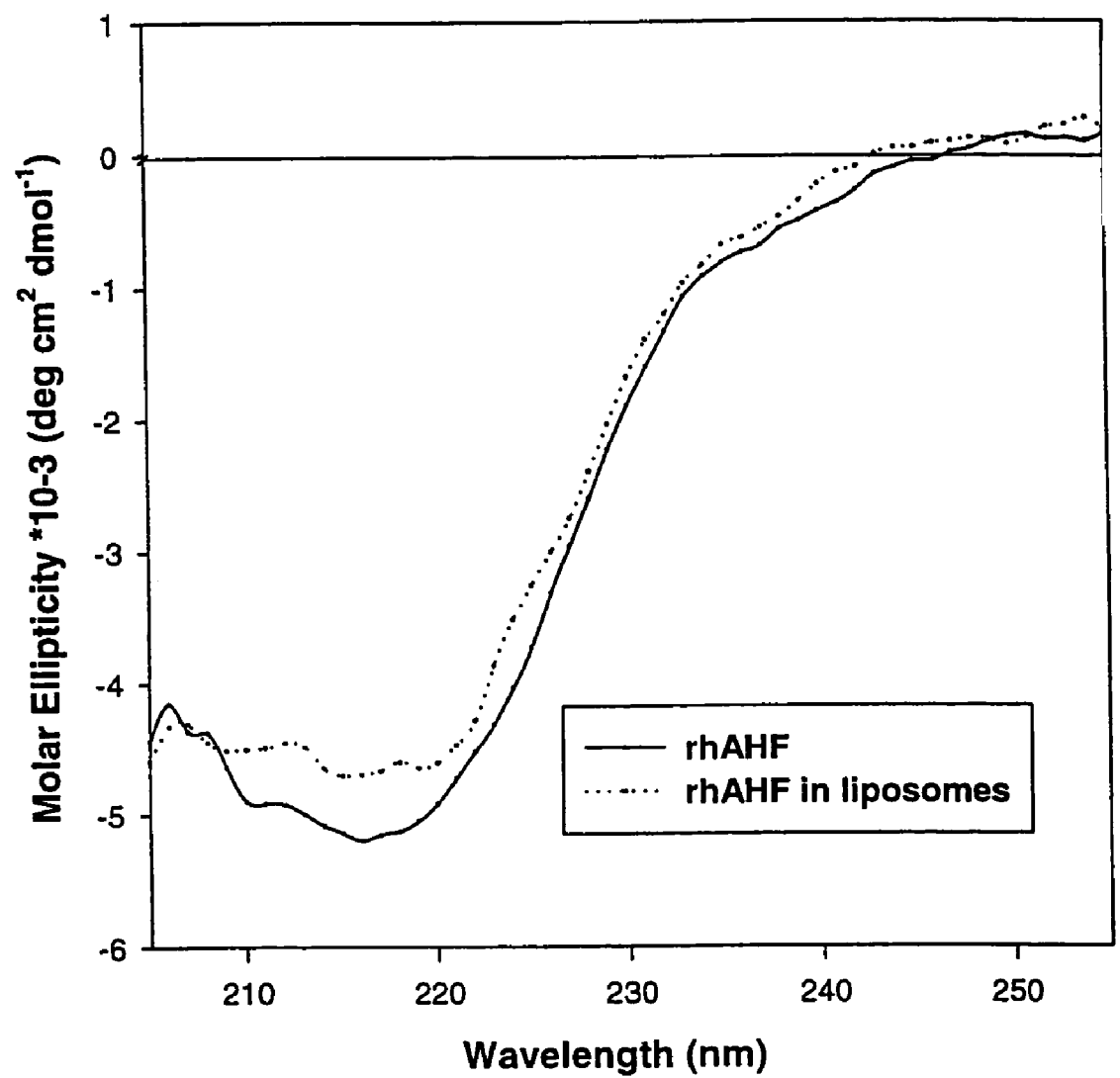
FIG. 10 is a graph of the molar ellipticity of rhAHF and rhAHF in liposomes.

Though it has been documented that AHF binds strongly to PS containing phospholipids in vivo, not much is known about the nature of interaction and molecular characteristics of the complex between PS containing liposomes and AHF. In order to understand the nature of this interaction, preliminary spectral studies were carried out. Conformation of factor VIII in the presence of liposomes examined by far-UV CD is shown in FIG. 10. The CD spectrum of protein in its native conformation is given for comparison (FIG. 10). In the native state, the protein exists predominantly in beta sheet conformation. The CD spectrum of liposome-associated rhAHF displayed a less intense negative band at 215 nm and a small red shift indicating a change in the conformation of the native protein.

Change in the Trp fluorescence of the protein was also followed in the presence of the liposomes as a means to probe the conformational state of the protein. In the presence of liposomes, an increase in fluorescence intensity was observed relative to that of the protein sample in the absence of liposomes. In addition, the Trp emission spectrum was blue-shifted relative to that of the native protein, though the observed shift was very small, most likely as a result of interaction of the non-polar region of the protein with the liposomal membrane. This interaction might offer shielding for the fluorophore containing domains from the external environment and may prevent aggregation of the protein.

Example 36

Effect of Liposomes on Equilibrium Refolding of rhAHF

In order to get an insight into the effect of liposomes on the unfolding and refolding pathway of the protein and understand the role of intermediates, equilibrium refolding studies of factor VIII were carried out under controlled heating and recooling conditions at different temperatures in the presence and absence of liposomes.

Figure 11A:
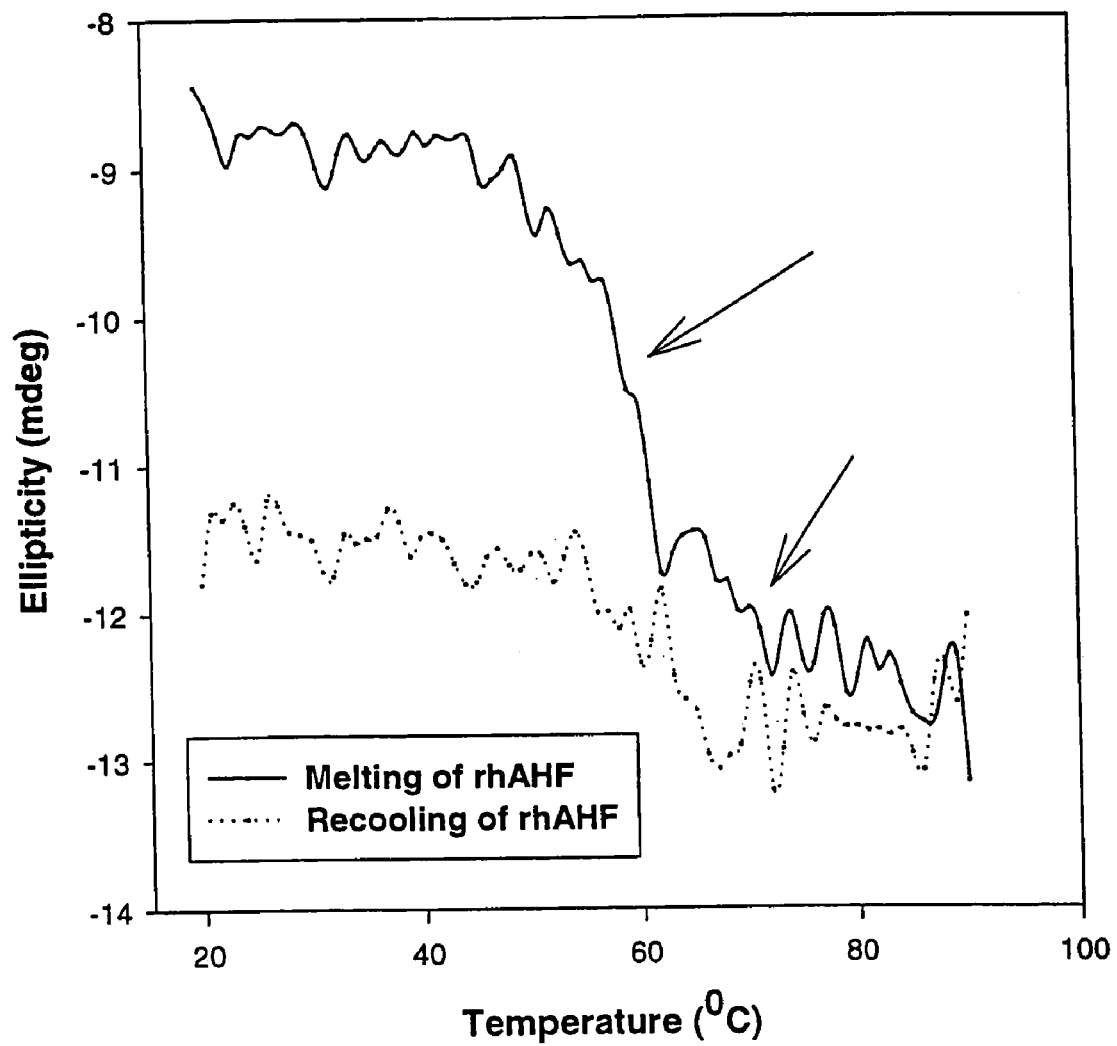
FIG. 11A is a graph showing the controlled heating and recooling of rhAHF in the appropriate buffer carried out over the temperature range of from 20° C. to 90° C. in the absence of liposomes.
Figure 11B:
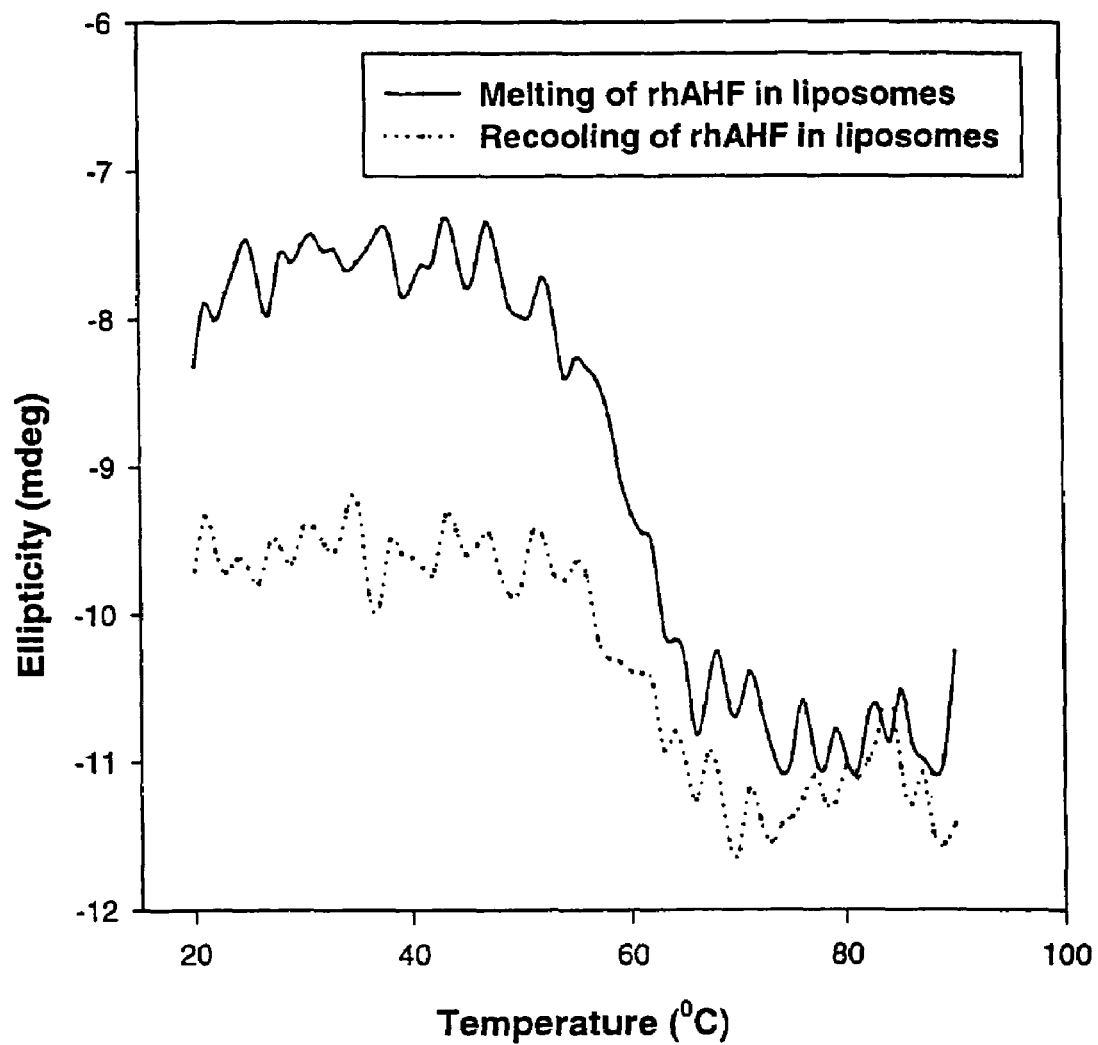
FIG. 11B is a graph showing the controlled heating and recooling of rhAHF in the appropriate buffer carried out over the temperature range of from 20° C. to 90° C. in the presence of liposomes.

FIG. 11A shows the melting and recooling of the secondary structure of the protein in the absence of liposomes. With increasing temperature, there were significant changes in the spectral characteristics. The melting as already described appeared to occur in two stages; a prominent transition with a Tm of from about 60° C. to about 62° C. and a very broad transition at about 70° C. The formation of intermolecular β-strands was prominent at temperatures $\geq 65°$ C. and there was a significant red shift in the far-UV CD spectrum accompanied by broadening of the 215 nm negative-band and occurrence of a positive band in the range of from 200 nm to 210 nm. On recooling the thermally denatured sample, there was no recovery of the native like secondary structure and broadened band at 215 nm was persistent. In the present of liposomes, as observed in FIG. 11B, the melting of the secondary structure again appeared to occur in two stages. While the first transition was similar to the one observed for the native protein, the second transition occurred over a broader temperature range. This may possibly be the result of the liposomes forming a complex with the protein. On re-cooling, the denatured protein in the presence of liposomes appeared to recover few of its native-like secondary structural features (FIG. 11B). Further, fluorescence studies validated the CD data, where the protein on re-cooling in the presence of liposomes showed significant recovery in intensity from about 48% to about 50% while the free protein showed only from about 20% to about 30% recovery in fluorescence intensity. The re-cooled protein in the presence of liposomes was also found to be marginally more active in comparison to the free protein.

In these experiments, the liposome based formulation was achieved by engineering a complex formation between AHF and the phosphatidyl serine (PS) head group containing liposomes. This complex was stabilized through hydrophobic interactions between liposomes and specific intermediate states in the protein conditions including 37° C. and 10-20% ethanol, exploiting the chaperone like molecular characteristics of the lipid assembly. The complexed intermediate also aids in refolding of the protein to its native state. The association of the liposome with the AHF protein resulted in increased stability, preventing aggregation (Table 2).

TABLE 2

Percent AHF Protein Associated Using Conventional and Present Technology

| Sample | % Protein associated |
|---|---|
| Conventional method | 49 (n = 1) to 45.5 ± 11.5 (n = 4) |
| Present methodology | 71.3 (n = 1) to 60.25 ± 7.27 (n = 4) |

The liposome loaded protein was separated from the free factor VIII by rapid sedimentation as describe previously (Gilbert et al., *J. Biol. Chem.* 266:815-822 (1990), which is hereby incorporated by reference in its entirety). The complex was spun at a rate of 15,000 g at 4° C. for 45 minutes. The supernatant and the resuspended pellets were analyzed by fluorescence spectroscopy. The unbound protein was separated from liposome bound protein by dextran centrifugation gradient. The samples were spun at 185,000 g for 30 min using SW50.1 Beckman rotor. The samples were analyzed by fluorescence and activity assay to determine the encapsulation efficiency.

The molecular association prepared in accordance with the present invention showed comparable activity to present conventionally administered formulations as shown by the activity data in Table 3.

TABLE 3

Activity Data

| Sample | Concentration based on activity (units/ml) |
|---|---|
| Free AHF Protein | 23.1 |
| Protein + liposome (conventional method) | 16.3 |
| Protein + liposome (present methodology) | 21.6 |

In order to increase the bioavailability of AHF, the complex/delivery vehicle was coated with polyethylene glycol using PEG-phosphatidyl ethanolamine as one of the lipid components in liposomes. This also addresses the immunogenicity problems by providing stealth like properties to the protein-lipid complex.

It has been documented that partial unfolding of the protein results in increased exposure of hydrophobic domains and promotes aggregation (Balasubramanian et al., *Pharm. Res.* 17:344-350 (2000), which is hereby incorporated by reference in its entirety). Hence, thermal denaturation studies of rhAHF were carried out to understand the subtleties involved in the unfolding process and its contribution towards physical destabilization. The melting of the protein was a multistage process and small changes observed in the secondary structure coupled with progressive loss of tertiary structure as the unfolding proceeded, suggested the transition of the native conformation of the protein to structured intermediate state(s). The data here suggests the existence of at least three "structured intermediate" states and such changes can cause protein inactivation by promoting aggregation. Further, analysis based on the equilibrium refolding studies indicated that while the formation of the intermediate state $SI_1$ was reversible, appearance of $SI_2$ and $SI_3$ in the unfolding pathway resulted in the protein loosing its structure irreversibly. The above observations suggest that intermediate state(s) formation occurring after or coinciding with the first major transition could possibly result in irreversible loss of protein structure (as shown in the schematic representation of FIG. 12) leading to precipitation of the protein.

The conformation of the AHF protein as determined by fluorescence spectroscopy indicates that sufficient exposure of hydrophobic domains occur in the temperature range of from 50° C. to 65° C. Such exposure can accelerate the aggregation process. Also, CD data indicate that the formation of intermolecular β-strands occurs at elevated temperatures. These observations lead to the hypothesis that the aggregates could possibly be stabilized by intermolecular β-strands and such stabilization in turn could promote precipitation over a period of time. Indeed, it has been documented that intermolecular β-strands mediate physical instability in proteins (Hilbich et al., *J. Mol. Biol.* 218:149-163 (1991); Hammarstrom et al., *J. Biol. Chem.* 274:32897-32903 (1999), which are hereby incorporated by reference in their entirety).

A very common approach to counter physical instability problems in proteins has been to use excipients (Tsai et al., *Pharm. Res.* 10:649-659 (1993); Carpenter et al., *Pharm. Res.* 14:969-975 (1997), which are hereby incorporated by reference in their entirety). However, the typical excipients used have been chosen empirically and the rationale underlying the formulation design assumes protein unfolding to be a two stage process (i.e., at any chosen time in the unfolding process, there exist only two kinds of populations; folded and unfolded molecules). While this might be valid for small proteins such as lysozyme and cytochrome C, such an assumption is an over simplification of the complex nature of the problem for multi-domain proteins like rhAHF. The studies of the present invention clearly suggest a multistage unfolding process and this can have profound implications. It has been found that the choice of an excipient should be based on its preferential interaction to the partially folded structures as such interactions can possibly enhance the ability of the excipient to guide these structures back to the native state.

Liposomes have previously been shown to stabilize protein against aggregation by preferentially interacting with the intermediate structures (Balasubramanian et al., *Pharm. Res.* 17:344-350 (2000), which is hereby incorporated by reference in its entirety). As AHF has been shown to bind strongly to PS containing phospholipids in vivo, PS containing liposomes were used to characterize the interaction with the protein. It has been documented that the presence of PS in membranes is essential for mediation of AHF binding (Gilbert et al., *Biochemistry* 32:9577-9585 (1993), which is hereby incorporated by reference in its entirety). Also, the PS binding site has been localized to the C2 domain, which is part of the light chain of AHF, though not much is known about the spatial orientation of the other five domains (Foster et al., Blood 75:1999-2004 (1990), which is hereby incorporated by reference in its entirety). However, based on a model proposed for the interaction of coagulation factor V (fV)(Gilbert et al., *J. Biol. Chem.* 265:815-822 (1990); Kalafatis et al., *Biochemistry* 33:486-493 (1994); Lecompte et al., *J. Biol. Chem.* 269:1905-1910, which are hereby incorporated by reference in their entirety), (a rhAHF homologue) with phospholipid, it has been proposed that regions other than C2 domain sequence may also be involved in membrane binding (Saenko et al., *J. Biol. Chem.* 270:13826-13833 (1995), which is hereby incorporated by reference in its entirety). Though the exact nature of this interaction is not known it is envisioned that PS containing liposomes interact with the protein, inducing conformational changes, resulting in the intercalation of the hydrophobic regions of C2 domain of the protein into the bilayer membrane. The polar head groups probably interact with the hydrophilic regions, offering additional stability to the complex. Further, it is speculated that the liposomes may provide a hydrophobic environment to the unfolding protein, thereby interacting preferentially with the partially folded structures and preventing intermolecular association. Initial spectral characterization studies suggest that the interaction of the liposomes with the protein appears to be dependent on the nature of the intermediate state as reflected in the reversibility associated with these intermediate states. In the presence of liposomes, while the formation of $SI_1$ was completely reversible, appearance of $SI_2$ resulted in irreversible loss of protein structure. However, there was partial recovery of the native-like features following formation of $SI_3$. It is also reasoned that the association with the PS containing liposomes induces the native structure of the protein to adopt a "non-native" like conformation and probably plays an important role in the unfolding/refolding process. Assuming that the protein sub-units in the heavy and light chains melt in a particular sequence during the denaturation process, in the event of liposomes binding to C2, this sequential melting of the sub-units might be altered. This is reflected in the observation from the fluorescence and far-UV CD studies that suggests that the protein, in the presence of liposomes, appear to take a different unfolding/refolding pathway. If this is true, then the lipid molecules associated with the protein might also be involved in guiding the protein towards its native state. Nevertheless, irrespective of the nature of the complex, this study gives a perspective to address the formulation issues concerning this complex protein and is discussed further infra.

It has been reported that the C2 domain of the protein is involved in high affinity interaction with the phospholipids present on the surface of the platelets (Foster et al., *Blood* 75:1999-2004 (1990), which is hereby incorporated by reference in its entirety). Further, it has been shown that inhibitors against the C2 domain are primarily responsible for neutralizing AHF activity in vivo (Scandella et al., *Throm. Res.* 101:377-385 (2001), which is hereby incorporated by reference in its entirety). The liposomal rAHF dispersions produced in this invention shield the epitope regions of the protein to reduce immune response and the antigenicity. In order to determine specifically whether the C2 domain is shielded in liposomes, an ELISA ("enzyme-linked immunosorbent assay") using C2 domain specific antibodies was prepared. Protein bound liposomes were coated onto Nunc Maxicorp plates by incubating overnight at 4° C. in carbonate buffer. The antibody binding (as measured by OD) was found to be far less for the liposome bound protein than for free protein, indicating the epitope region is not available for the antibody binding. In addition to ELISA, fluorescence quenching by acrylamide was carried out to determine the accessibility of fluorophore on the protein to collisional quenchers. This data would provide information on the location of the protein in liposomes. The quenching experiment indicated that the lipidic rhAHF produced by this procedure indicated that the quenching efficiency of 0.2 M acrylamide is 38% lower for liposome bound protein than that for the free protein. The results support the ELISA assay in which the part of the protein molecule is shielded as a result of lipid binding.

Figure 13:
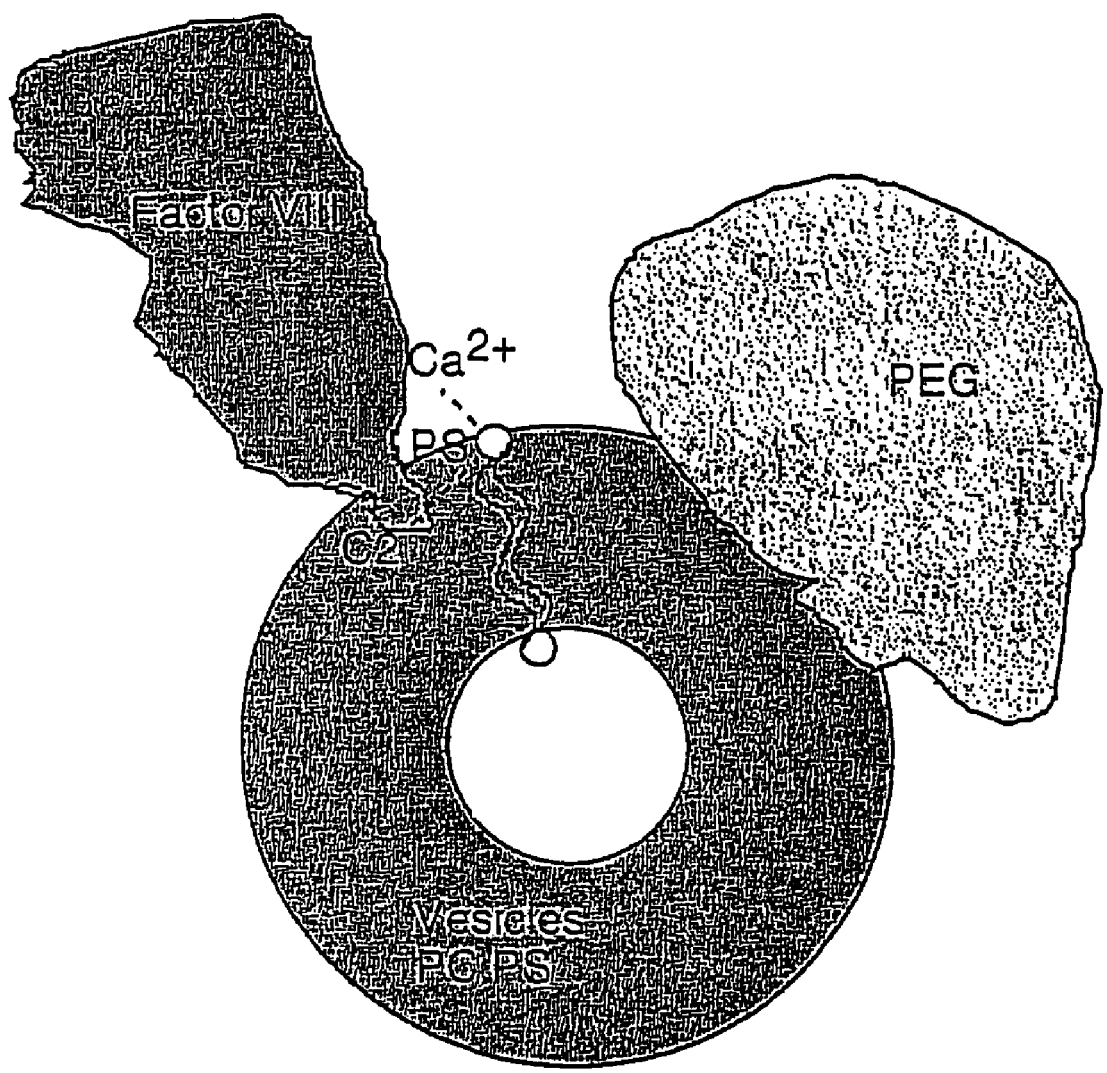
FIG. 13 is a schematic representation of the rhAHF-liposome complex based delivery vehicle of the present invention.

The observations supra illustrate the desirable features of using liposomes as a stabilizer in rhAHF formulations. The complex formation between the protein and lipid may further enhance the stability of the protein in vivo by preventing enzyme(s) inactivation. Further, surface modified liposomes can also be used as a safe delivery vehicle (Woodle et al., *Biochim. Biophys. Acta* 1105:193-200 (1992), which is hereby incorporated by reference in its entirety). One of the approaches to achieve this has been to coat the surface with hydrophilic polymers such as polyethyleneglycol (PEG)(Klibanov et al., *FEBS Lett.* 268:235-237 (1990), which is hereby incorporated by reference in its entirety). PEGylated liposomes have also been shown to circulate in the blood for a longer time, by evading the RES system (Lasic et al., *Biochim. Biophys. Acta* 1070:187-192 (1991); Papahadjopoulos et al., *Proc. Natl. Acad. Sci. USA* 8:11460-4 (1991), which are hereby incorporated by reference in their entirety). The feasibility of using PEGylated liposomes as a means to (1) promote complex formation and stabilize the protein (FIG. 13) and (2) as a vehicle to deliver the rhAHF in vivo thereby increasing its circulation time has been explored. Preliminary studies have shown that the activity of the protein associated with liposomes is comparable to that of the free protein. Heating in the presence of the solvent will expedite the desired conformational changes required for the liposomal association of the AHF protein.

Example 37

Complexation of Interferon-Gamma

20 μg of interferon-gamma was dissolved in phosphate buffered saline containing 10% ethanol to generate structures that are suitable for triggered loading. The CD spectra of interferon-gamma in the presence and in the absence of ethanol at 25° C. and 40° C. showed that conformation of the protein was not altered significantly in the presence of ethanol. The protein retained substantial secondary and tertiary structures at this ethanol concentration, which suggests that the structures generated are not traditional intermediates such as molten globule. Further, the Tm based on thermal melting of Interferon-gamma in PBS saline was found to be 56.7° C. and it decreased to 43.8° C. in the presence of ethanol further suggesting the clustering of ethanol molecules around hydrophobic groups. This molecular structure is suitable for engineering a hydrophobic interaction between protein and liposomes. The structure generated in the presence of 10% ethanol at 40° C. was utilized to encapsulate in liposomes made of DMPC:PG mixtures. Approximately 6.75 mg of Dimyristoyl Phosphatidyl Choline (DMPC) and 0.675 mg of Dimyristoyl Phosphatidyl Glycerol (DMPG) in chloroform solution was evaporated to form a thin film around the sides of a round bottomed flask. The film was hydrated using 25 μg of interferon-gamma dissolved in phosphate buffered saline, in the presence and in the absence of 10% ethanol at 25° C. and 40° C. The ethanol in samples was evaporated using jet of dry nitrogen and was replaced with phosphate buffered saline. The free protein was separated from liposome-associated protein by Dextran density gradient. Protein and liposome samples in different gradient were analyzed by BCA protein assay kit, fluorescence or by measuring absorbance at 280 nm to determine the protein associated with liposomes. The structure suitable for triggered loading (in the presence of 10% ethanol at 40° C.) mediated higher liposome association (typically 6-10% higher) compared to native state.

Example 38

Complexation of Factor VIII

50 μg of Factor VIII was dissolved in TRIS buffer (300 mM NaCl, 25 mM Tris, 5 mM CaCl2.2H2O, pH=7.0) containing 10% and 20% ethanol to generate structures that are suitable for triggered loading. Full length or B-domain deleted FVIII was expressed in COS-7 or CHO cells and chromatographically purified. The CD spectra of Factor VIII in the presence and in the absence of ethanol at 25° C. and 40° C. showed that conformation of the protein was not altered significantly in the presence of ethanol. The protein retained substantial secondary and tertiary structures at this ethanol concentration suggesting that the structures generated are not traditional intermediates such as molten globule. Further, the Tm based on thermal melting of Factor VIII was found to be 60.1° C. and it decreased to 51.5° C. in the presence of ethanol further suggesting the clustering of ethanol molecules around hydrophobic groups. This molecular structure is suitable for engineering a hydrophobic interaction between protein and liposomes. The structure generated in the presence of 10% ethanol at 40° C. was utilized to encapsulate in liposomes made of Dimyristoyl Phosphatidyl Choline (DMPC): Phosphatidyl Serine (PS) mixtures. Approximately 1.69 mg of DMPC and 0.868 mg of brain PS in chloroform solution was evaporated to form a thin film around the sides of a round bottomed flask. The film was hydrated using TRIS buffer and was extruded using 200 micron polycarbonate filers. The protein was associated with liposomes in the presence and in the absence of ethanol at 20° C. and 37° C. The ethanol in samples was evaporated using jet of dry nitrogen and was replaced with phosphate buffered saline. The free protein was separated from liposome-associated protein by Dextran density gradient. Protein in different gradient fractions was analyzed by BCA protein assay, fluorescence or by absorbance at 280 nm to determine the % protein association with liposomes. The structure suitable for triggered loading, for e.g., in the presence of 10% ethanol at 40° C. resulted in, 57% (fluorescence assay, n=2) of the protein. The protein association mediated by native state for e.g, at 37° C. was found to be 45.2±16.8 (n=16) based on activity assay. However, it is appropriate to mention that the interaction mediated under these experimental conditions may be different and may not be compared for association efficiency. Liposome composition also plays an important role in protein association. For example, native state of FVIII readily interacts with PS containing liposomes due to electrostatic interaction. In the presence of ethanol, the hydrophobic interaction may mediate protein association with liposomes that may interfere with electrostatic interaction.

While the invention has been described with preferred embodiments, it is to be understood that variations and modifications may be resorted to as will be apparent to those skilled in the art. Such variations and modifications are to be considered within the purview and the scope of the claims appended hereto.

What is claimed is:

1. A method for complexing a protein having biological activity with liposomes, said method comprising:

(a) providing a protein;

(b) altering the conformational state of the protein to expose hydrophobic domains therein by contacting said protein with a mixture of water and ethanol at a concentration of 10% (v/v) at a temperature of 37° C. or higher;

(c) separately preparing liposomes comprising phospholipids selected from the group consisting of phosphatidylserine (PS), phosphatidylchloline (PC), phosphatidylethanolamine (PE), phosphatidylglycerol (PG) and combinations thereof;

(d) contacting the liposomes from (c) with the protein having an altered conformational state from (b); and (e) at least partially reversing said altered conformational state of the protein complexed with the liposomes from (d) by removal of the ethanol from the mixture;

wherein the protein has biological activity.

2. The method according to claim 1, wherein the mixture has a pH range from 7.0 to 7.4.

3. The method according to claim 1, wherein said contacting is carried out at a temperature of 40° C. to 74° C.

4. The method according to claim 1, wherein said contacting is carried out at a temperature of 70° C. to 74° C.

5. The method according to claim 3, wherein said contacting is carried out at a temperature of 58° C. to 62° C.

6. The method according to claim 3, wherein said contacting is carried out at a temperature of 40° C.

7. The method according to claim 1, wherein the protein is lysozyme.

8. The method according to claim 1, wherein the protein is interferon-gamma.

9. The method according to claim 1, wherein the protein is antihemophilic factor (AHF).

10. The method according to claim 1, wherein said reversing comprises dialysis.

11. The method according to claim 1, wherein said altering comprises unfolding the protein.

12. The method according to claim 1, wherein said protein from step (b) has secondary and tertiary structural features.

13. The method according to claim 1, wherein said reversing comprises refolding the protein.

14. The method according to claim 1, wherein the mixture is an ethanol-phosphate buffered saline solution mixture.

15. The method according to claim 1, wherein the ethanol is denatured ethanol.

16. The method according to claim 15, wherein the ethanol is 190 proof grade ethanol or 200 proof grade ethanol.

* * * * *